(12) United States Patent
Bonini et al.

(10) Patent No.: US 9,643,985 B2
(45) Date of Patent: May 9, 2017

(54) PCL COMPOUNDS, COMPOSITIONS, AND METHODS OF USE THEREOF

(71) Applicant: The Board Of Trustees Of The University Of Illinois, Urbana, IL (US)

(72) Inventors: Marcelo Bonini, Chicago, IL (US); Nathan A. Sieracki, Chicago, IL (US); Alexander V. Lyubimov, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 14/768,525

(22) PCT Filed: Feb. 18, 2014

(86) PCT No.: PCT/US2014/016915
§ 371 (c)(1),
(2) Date: Aug. 18, 2015

(87) PCT Pub. No.: WO2014/127360
PCT Pub. Date: Aug. 21, 2014

(65) Prior Publication Data
US 2015/0376680 A1 Dec. 31, 2015

Related U.S. Application Data

(60) Provisional application No. 61/765,849, filed on Feb. 18, 2013.

(51) Int. Cl.
*C07F 5/02* (2006.01)
*C07D 417/04* (2006.01)
*C12Q 1/66* (2006.01)

(52) U.S. Cl.
CPC ............ *C07F 5/025* (2013.01); *C07D 417/04* (2013.01); *C07F 5/02* (2013.01); *C12Q 1/66* (2013.01); *G01N 2800/06* (2013.01); *G01N 2800/40* (2013.01)

(58) Field of Classification Search
CPC .................................. C07F 5/025; C07F 5/02
See application file for complete search history.

(56) References Cited

FOREIGN PATENT DOCUMENTS

WO 2011/133800 10/2011
WO WO 2011/133800 A1 * 10/2011 ............... A61B 5/00

OTHER PUBLICATIONS

International Search Report, issued Jun. 23, 2014, in connection with corresponding International Patent Application No. PCT/US2014/016915, 4 pages.

Alvarez et al., "Kinetics of peroxynitrite reaction with amino acids and human serum albumin," J. Biol. Chem. 274 (4):842-8 (Jan. 1999).
Alvarez et al., "Inactivation of human Cu,Zn superoxide dismutase by peroxynitrite and formation of histidinyl radical," Free Radic. Biol. Med. 37(6):813-22 (Sep. 2004).
Augusto et al., "Spin-trapping studies of peroxynitrite decomposition and of 3-morpholinosydnonimine N-ethylcarbamide autooxidation: direct evidence for metal-independent formation of free radical intermediates," Arch. Biochem. Biophys. 310(1):118-25 (Apr. 1994).
Augusto et al., "Nitrogen dioxide and carbonate radical anion: two emerging radicals in biology," Free Radic. Biol. Med. 32(9):841-59 (May 2002).
Bayir et al., "Neuronal NOS-mediated nitration and inactivation of manganese superoxide dismutase in brain after experimental and human brain injury," J. Neurochem. 101(1):168-81 (Apr. 2007).
Beckman et al., "Apparent hydroxyl radical production by peroxynitrite: implications for endothelial injury from nitric oxide and superoxide," Proc. Natl. Acad. Sci. U.S.A. 87(4):1620-4 (Feb. 1990).
Bonini et al., "Direct EPR detection of the carbonate radical anion produced from peroxynitrite and carbon dioxide," J. Biol. Chem. 274(16):10802-6 (Apr. 1999).
Buzzeo et al., "Kinetic Analysis of the Reaction between Electrogenerated Superoxide and Carbon Dioxide in the Room Temperature Ionic Liquids 1-Ethyl-3-methylimidazolium Bis(trifluoromethylsulfonyl)imide and Hexyltriethylammonium Bis(trifluoromethylsulfonyl)imide," J. Phys. Chem. B. 108(12):3947-54 (Feb. 2004).
Castro et al., "Aconitase is readily inactivated by peroxynitrite, but not by its precursor, nitric oxide," J. Biol. Chem. 269(47):29409-15 (Nov. 1994).
Di Mascio et al., "Reaction of peroxynitrite and hydrogen peroxide to produce singlet molecular oxygen (1Δg)," Methods Enzymol. 269:395-400 (1996).
Foyer et al., "Ascorbate and glutathione: the heart of the redox hub," Plant Physiol. 155(1):2-18 (Jan. 2011).
Halliwell, "What nitrates tyrosine? Is nitrotyrosine specific as a biomarker of peroxynitrite formation in vivo?," FEBS Lett. 411(2-3)157-60 (Jul. 1997).
Kelm et al., "The nitric oxide/superoxide assay. Insights into the biological chemistry of the NO/O-2. interaction," J. Biol. Chem. 272(15):9922-32 (Apr. 1997).
Laursen et al., "Endothelial regulation of vasomotion in apoE-deficient mice: implications for interactions between peroxynitrite and tetrahydrobiopterin," Circulation 103(9):1282-8 (Mar. 2001).
Liaudet et al., "Role of peroxynitrite in the redox regulation of cell signal transduction pathways," Front. Biosci. (Landmark Ed.) 14:4809-14 (Jan. 2009).

(Continued)

Primary Examiner — Joseph Kosack
(74) Attorney, Agent, or Firm — McDonnell Boehnen Hulbert & Berghoff LLP

(57) ABSTRACT

Disclosed herein are compounds useful for detecting oxidants in a living cell, in a multicellular organism, or in a cell-free sample. In particular, disclosed herein are bioluminescent reporter compounds, and more particularly, fluorinated peroxy-caged-luciferin (PCL) compounds, compositions comprising such compounds, methods of using such compounds and compositions, and processes for preparing such compounds. Also disclosed herein are kits and methods for detecting and measuring peroxynitrite, and optionally, additional oxidants in a living cell, in a multicellular organism, or in a cell-free sample.

18 Claims, 21 Drawing Sheets

(56) References Cited

OTHER PUBLICATIONS

Linares et al., "Role of peroxynitrite in macrophage microbicidal mechanisms in vivo revealed by protein nitration and hydroxylation," Free Radic. Biol. Med. 30(11)1234-42 (Jun. 2001).

Lymar et al., "Rapid reaction between peroxonitrite ion and carbon dioxide: Implications for biological activity," J. Am. Chem. Soc. 117(34):8867-8 (Aug. 1995).

Martin-Romero et al., "The NADH oxidase activity of the plasma membrane of synaptosomes is a major source of superoxide anion and is inhibited by peroxynitrite," J. Neurochem. 82(3):604-14 (Aug. 2002).

Masutani et al., "The thioredoxin system in retroviral infection and apoptosis," Cell Death Differ. 12(Suppl 1):991-8 (Aug. 2005).

Pfeiffer et al., "Metabolic fate of peroxynitrite in aqueous solution. Reaction with nitric oxide and pH-dependent decomposition to nitrite and oxygen in a 2:1 stoichiometry," J. Biol. Chem. 272(6):3465-70 (Feb. 1997).

Pfeiffer et al., "Protein tyrosine nitration in cytokine-activated murine macrophages. Involvement of a peroxidase/nitrite pathway rather than peroxynitrite," J. Biol. Chem. 276(36):34051-8 (Jun. 2001).

Pfeiffer et al., "Protein tyrosine nitration in mouse peritoneal macrophages activated in vitro and in vivo: evidence against an essential role of peroxynitrite," FASEB J. 15(13):2355-64 (Nov. 2001).

Roberts et al., "Nucleophilic oxygenation of carbon dioxide by superoxide ion in aprotic media to form the peroxydicarbonate(2-) ion species," J. Am. Chem. Soc. 106(17):4667-70 (Aug. 1984).

Robinson et al., "Synthesis of peroxynitrite from nitrite and hydrogen peroxide," Methods Enymol. 396:207-14 (1995).

Rubbo et al., "Nitric oxide regulation of superoxide and peroxynitrite-dependent lipid peroxidation. Formation of novel nitrogen-containing oxidized lipid derivatives," J. Biol. Chem. 269(42):26066-75 (Oct. 1994).

Schrammel et al, "Activation of soluble guanylyl cyclase by the nitrovasodilator 3-morpholinosydnonimine involves formation of S-nitrosoglutathione," Mol. Pharmacol. 54(1):207-12 (Jul. 1998).

Sieracki et al., "Bioluminescent detection of peroxynitrite with a boronic acid-caged luciferin," Free Radic. Biol. Med. 61(C):40-50 (Aug. 2013).

Sikora et al., "Direct oxidation of boronates by peroxynitrite: mechanism and implications in fluorescence imaging of peroxynitrite," Free Radic. Biol. Med. 47(10):1401-7 (Nov. 2009).

Sikora et al., "Reaction between peroxynitrite and boronates: EPR spin-trapping, HPLC Analyses, and quantum mechanical study of the free radical pathway," Chem. Res. Toxicol. 24(5):687-97 (May 2011).

Stadler, "Peroxynitrite-driven mechanisms in diabetes and insulin resistance—the latest advances," Curr. Med. Chem. 18(2):280-90 (2011).

Szabó et al., "Peroxynitrite: biochemistry, pathophysiology and development of therapeutics," Nat. Rev. Drug Discov. 6(8):662-80 (Aug. 2007).

Takakura et al., "Rapid and irreversible inactivation of protein tyrosine phosphatases PTP1B, CD45, and LAR by peroxynitrite," Arch. Biochem. Biophys. 369(2):197-207 (Sep. 1999).

Tiago et al., "Peroxynitrite-mediated oxidative modifications of myosin and implications on structure and function," Free Radic. Res. 44(11)1317-27 (Nov. 2010).

Van De Bittner et al., "In vivo imaging of hydrogen peroxide production in a murine tumor model with a chemoselective bioluminescent reporter," Proc. Natl. Acad. Sci. U.S.A. 107(50):21316-21 (Dec. 2010).

Vásquez-Vivar, "Tetrahydrobiopterin, superoxide, and vascular dysfunction," Free Radic. Biol. Med. 47(8):1108-19 (Oct. 2009).

Wardman, "Fluorescent and luminescent probes for measurement of oxidative and nitrosative species in cells and tissues: progress, pitfalls, and prospects," Free Radic. Biol. Med. 43(7):995-1022 (Oct. 2007).

Yao et al., "A bioluminogenic substrate for in vivo imaging of beta-lactamase activity," Angew. Chem. Int. Ed. Engl. 46 (37):7031-4 (Aug. 2007).

Zhang et al., "Inhibition of Peroxynitrite-Mediated Oxidation of Glutathione by Carbon Dioxide," Arch. Biochem. Biophys. 339(1):183-9 (Mar. 1997).

Zhang et al., "The mechanism of the peroxynitrite-carbon dioxide reaction probed using tyrosine," Nitric Oxide 1 (4):301-7 (Aug. 1997).

Zielonka et al., "Peroxynitrite is the major species formed from different flux ratios of co-generated nitric oxide and superoxide: direct reaction with boronate-based fluorescent probe," J. Biol. Chem. 285(19):14210-6 (May 2010).

Zielonka et al., "Boronate probes as diagnostic tools for real time monitoring of peroxynitrite and hydroperoxides," Chem. Res. Toxicol. 25(9):1793-9 (Sep. 2012).

Zou et al., "Rapid reactions of peroxynitrite with heme-thiolate proteins as the basis for protection of prostacyclin synthase from inactivation by nitration," Arch. Biochem. Biophys. 376(1):149-55 (Apr. 2000).

\* cited by examiner

PCL COMPOUNDS, COMPOSITIONS, AND METHODS OF USE THEREOF

CROSS-REFERENCE TO RELATED APPLICATIONS

This application is a U.S. national stage application of International Application No. PCT/US2014/016915, filed Feb. 18, 2014, which claims the benefit of priority of U.S. Provisional Application No. 61/765,849, filed Feb. 18, 2013, the disclosures of both of which are incorporated by reference herein in their entireties.

BACKGROUND

Peroxynitrite (ONOO⁻/ONOOH) is a highly reactive biological oxidant formed under pathophysiologic conditions from the reaction of nitric oxide and superoxide radical anion. Peroxynitrite decomposes rapidly under physiological conditions to oxidizing intermediates, such as singlet oxygen ($^1O_2$), $.NO_2$ free radical, and .OH free radical, that can damage biological targets. Pathological consequences associated with damage to biological targets can include oxidizing or nitrating of proteins, lipids, or DNA. Peroxynitrite crosses lipid membranes at a rate significantly faster than the rates of other known oxidants, indicating that this oxidant can travel distances of cellular dimensions. Thus, even in the presence of biological membranes, peroxynitrite can have free access to cellular interiors. Peroxynitrite is also known to nitrate tyrosine residues in proteins, and to oxidize sulfhydryls, methionines and macromolecules such as, for example, metalloenzymes, DNA, and lipids.

Peroxynitrite has been implicated in a variety of diseases and conditions. These diseases and conditions include, e.g., Alzheimer's disease, Parkinson's disease, Huntington's disease, amyotrophic lateral sclerosis, dementia, atherosclerosis, post-infarction myocardial complications, arrhythmias, stroke, post-stroke tissue damage, acute respiratory disease syndrome, chronic obstructive pulmonary disease, pulmonary hypertension, vascular hypertension, cancer, ischemia-reperfusion injury, arthritis, inflammatory bowel disease, ulcerative colitis, AIDS, hepatitis, septic shock, chronic rejection of renal grafts, diabetes, gout, pancreatitis, meningitis, influenza, lupus, and radiation induced gastrointestinal injury.

Despite the relevance of peroxynitrite in biological systems and in the pathophysiology of several diseases, the study of this oxidant has been hindered by a lack of reliable and specific detection methods. Examples of known methods for detecting peroxynitrite include a method of detecting 8-nitroguanine produced by nitration of guanine, or nitrotyrosine produced by nitration of tyrosine, and a method of detecting singlet oxygen produced by reaction of peroxynitrite and hydrogen peroxide ($H_2O_2$) on the basis of light emission at 1.3 μm (Di Mascio et al., *Methods Enzymol.* 1996, 269:395-400). (Note that peroxide anion, OOH⁻, is likely the true reactive species in the case of hydrogen peroxide.) Although the first method achieves high specificity and has been widely used, that method requires the use of HPLC or immunostaining using an antibody, and therefore peroxynitrite cannot be detected in real time. In addition to the aforementioned two methods, there is a chemiluminescence method using luminol, and a fluorometric detection method using a 2',7'-dichlorodihydrofluorescein (DCFH) fluorescence probe to detect overall active oxygen species (Wardman, *Free Radic. Biol. Med.* 2007, 43(7):995-1022). These methods, however, fail to achieve specificity for peroxynitrite, and therefore reliable detection cannot be expected even if various inhibitors are used. For example, in the method using 2',7'-dichlorodihydrofluorescein (DCFH), DCFH reacts with both of nitrogen monoxide and superoxide to give an increase in fluorescence, and therefore it is impossible to distinguish whether peroxynitrite, nitrogen monoxide, or superoxide is detected.

Other chemical probes are known, but also suffer from a lack of specificity. For example, arylated fluorescein derivatives are known to be useful as fluorescent probes which do not react with nitrogen monoxide and superoxide. However, these probes not only react with peroxynitrite, but also react with reactive oxygen species such as hypochlorite ion and hydroxyl radical, and thus are not capable of achieving specific detection solely of peroxynitrite.

Accordingly, improved compounds, compositions, and methods for detecting and measuring peroxynitrite are needed that, inter alia, could be used to highly selectively visualize peroxynitrite in a living cell or tissue. For example, there is an ongoing need for non-invasive early markers of radiation induced gastrointestinal (GI) injury.

SUMMARY

The present invention provides certain advantages and advancements over the prior art. In particular, the invention provides compounds, compositions, and methods for non-invasively detecting oxidants, such as reactive oxygen species like peroxynitrite, in real time in living cells or tissues. In some embodiments, the invention provides compounds, compositions, and methods for highly selectively and non-invasively detecting or visualizing peroxynitrite in real time in living cells or tissues.

In one aspect, compounds having formula (I) are disclosed,

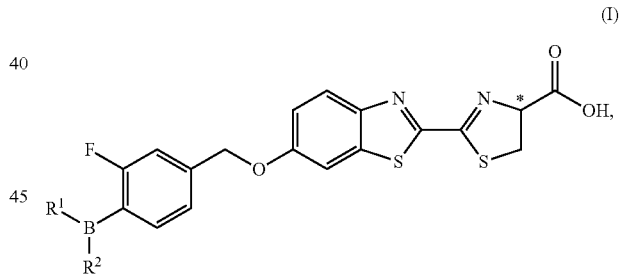

(I)

and pharmaceutically acceptable salts, esters, amides, prodrugs, and radiolabeled forms thereof, wherein $R^1$ and $R^2$ are each independently hydroxy or alkoxy, or $R^1$ and $R^2$ form together with the boron atom to which is attached an optionally substituted 5- to 7-membered dioxaborolanyl group; wherein * designates a stereocenter.

In another aspect, disclosed are compositions comprising a compound as disclosed herein and a pharmaceutically acceptable carrier or excipient. Preferably, the compositions are suitable for use in measuring and/or detecting peroxynitrite in a living cell or tissue.

In yet another aspect, disclosed are kits for use in measuring and/or detecting peroxynitrite in a living cell or tissue. Optionally, a kit can be configured to detect and/or measure additional oxidants, such as reactive oxygen species.

In another aspect, disclosed are methods for detecting and/or measuring peroxynitrite in a living cell or tissue. The disclosed methods include administering a compound of the present invention to a biological system and thereafter detecting and/or measuring bioluminescence resulting therefrom. Optionally, these methods include co-administration of a compound of the present invention with another bioluminescent reporter compound, such as peroxy-caged-luciferin-1 (PCL-1). Optionally, the methods include detecting and/or measuring the presence of reactive oxygen species, such as hydrogen peroxide, in the system.

In another aspect, using the compounds and methods disclosed herein, the signal generated by the reaction of compounds disclosed herein with peroxynitrite in a subject can be detected in the feces of the subject, thereby providing a convenient marker of radiation-induced GI injury. Accordingly, in certain embodiments, methods for detecting radiation induced gastrointestinal injury in a subject are provided, comprising administering to the subject one or more compounds of the invention and detecting a signal generated by reaction of the compounds of the invention with peroxynitrite in the feces of the subject.

The compounds, compositions, methods and processes are further described herein. These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, in which.

Figure 1:
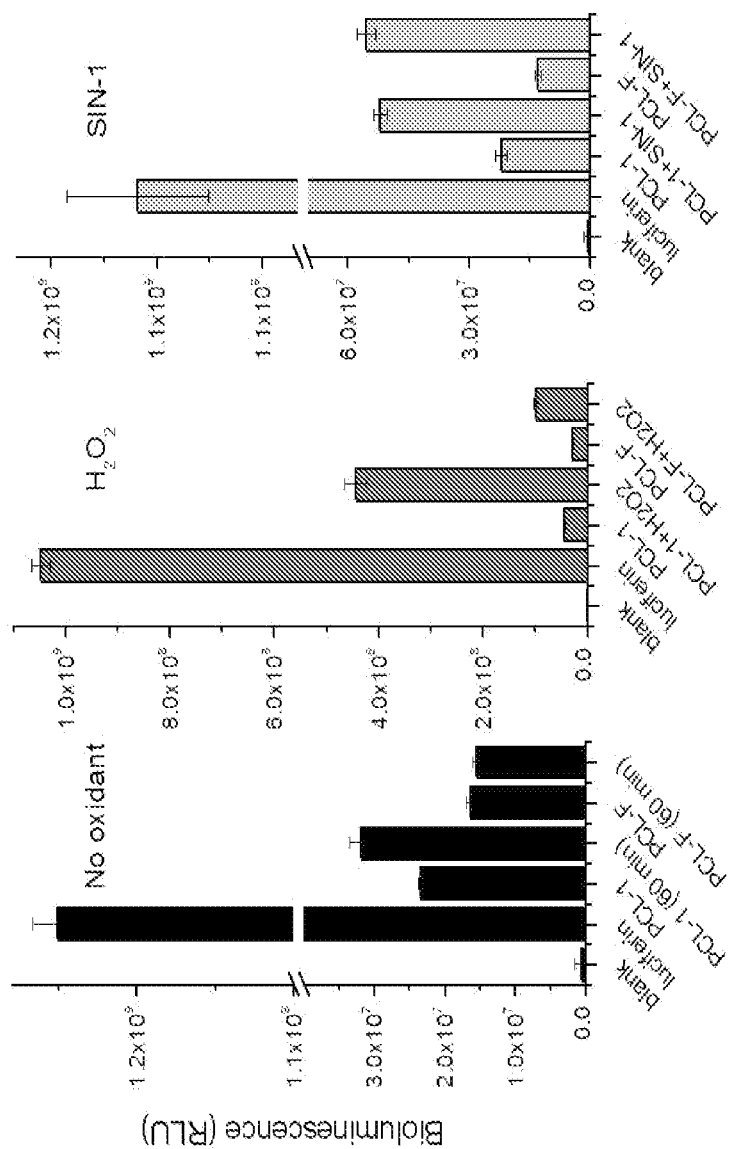
FIG. 1 shows a bioluminescence spectrum of PCL-F compared to a bioluminescence spectrum of PCL-1.

Skilled artisans will appreciate that elements in the figures are illustrated for simplicity and clarity and have not necessarily been drawn to scale. For example, the dimensions of some of the elements in the figures can be exaggerated relative to other elements to help improve understanding of the embodiment(s) of the present invention.

DETAILED DESCRIPTION

The present disclosure provides compounds, compositions, and methods for non-invasively detecting oxidants, such as peroxynitrite (ONOO$^-$/ONOOH), in real time in living cells or tissues. In some embodiments, provided herein are compounds, compositions, and methods for highly selectively and non-invasively detecting or visualizing peroxynitrite in real time in living cells or tissues.

Definition of Terms

Unless otherwise defined, all technical and scientific terms used herein have the same meaning as commonly understood by one of ordinary skill in the art. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein, the singular forms "a", "an", and "the" include plural referents unless the context clearly dictates otherwise. For example, reference to a "molecule" means one or more molecules.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "alkyl" refers to a linear or branched hydrocarbon radical having 1, 2, 3, 4, 5, 6, 7, 8, 9, or 10 carbons. Alkyl groups of the present invention include, but are not limited to, methyl, ethyl, n-propyl, isopropyl, n-butyl, iso-butyl, secondary-butyl, and tertiary-butyl. Alkyl groups of the present invention can be unsubstituted or substituted by one or more suitable substituents, preferably 1 to 3 suitable substituents, as defined above. Preferred alkyls include ($C_1$-$C_6$) alkyl, more preferred are ($C_1$-$C_4$) alkyl, and most preferred are methyl and ethyl.

As used herein, the term "alkoxy" refers to an alkyl group, as defined herein, appended to the parent molecular moiety through an oxygen atom.

As used herein, the term "hydroxy" refers to an —OH group.

As used herein, the term "dioxaborolanyl group" refers to an organic functional group comprising an O—B—O group, where the dioxaborolanyl group is appended to the parent molecular moiety through the boron atom. Examples of dioxoborolanyl groups include, but are not limited to, —B(OH)$_2$, —B(OCH$_3$)$_2$, —B(OCH$_2$CH$_3$)$_2$, —B(OCH$_2$CH$_2$CH$_3$),

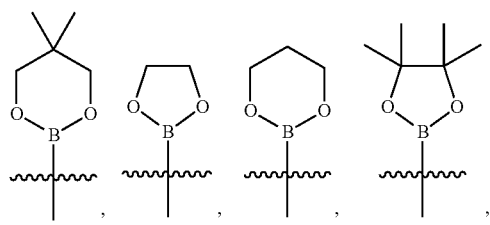

-continued

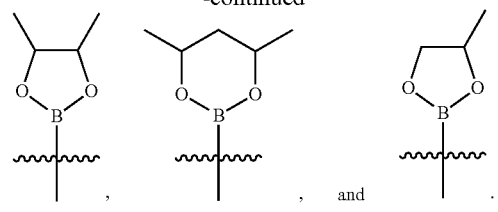

, and

In some embodiments, the compounds disclosed herein are formulated as a pharmaceutically acceptable salt. As used herein, the term "pharmaceutically acceptable salt" refers to a salt of a compound derived from the combination of the compound and a pharmaceutically acceptable organic or inorganic acid (acid addition salts) or a pharmaceutically acceptable organic or inorganic base (base addition salts) which retain the biological effectiveness and properties of the compounds of the present invention and which are not biologically or otherwise undesirable. Examples of pharmaceutically acceptable salts include but not limited to those described in for example: "Handbook of Pharmaceutical Salts, Properties, Selection, and Use," P. Heinrich Stahl and Camille G. Wermuth (Eds.), Published by VHCA (Switzerland) and Wiley-VCH (FRG), 2002. The compounds of the present invention can be used in either the free base or salt forms, with both forms being considered as being within the scope of the present invention.

Compounds

Compounds of the invention include peroxy-caged-luciferin (PCL) compounds. In one aspect, peroxy-caged-luciferin compounds of the present invention have formula (I),

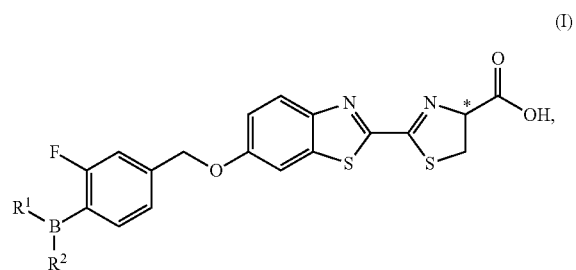

or a pharmaceutically acceptable salt, ester, amide, prodrug, or radiolabeled form thereof, wherein $R^1$ and $R^2$ are each independently selected from the group consisting of hydroxy and alkoxy, or $R^1$ and $R^2$ form together with the boron atom to which they are attached an optionally substituted 5- to 7-membered dioxaborolanyl group; and * designates a stereocenter.

In one embodiment, $R^1$ is hydroxy and $R^2$ is hydroxy. In another embodiment, $R^1$ is alkoxy and $R^2$ is alkoxy. In another embodiment, $R^1$ and $R^2$ form together with the boron atom to which they are attached an optionally substituted 5- to 7-membered dioxaborolanyl group. In a preferred embodiment, the dioxaborolanyl group is a 4,4,5,5-tetramethyl-1,3,2-dioxaborolan-2-yl group.

In one embodiment, the compound of formula (I) is racemic. In another embodiment, * designates a stereocenter having an (S)-configuration. In another embodiment, * designates a stereocenter having an (R)-configuration.

In one embodiment, the compound of formula (I) has the formula (I-A), (I-A)

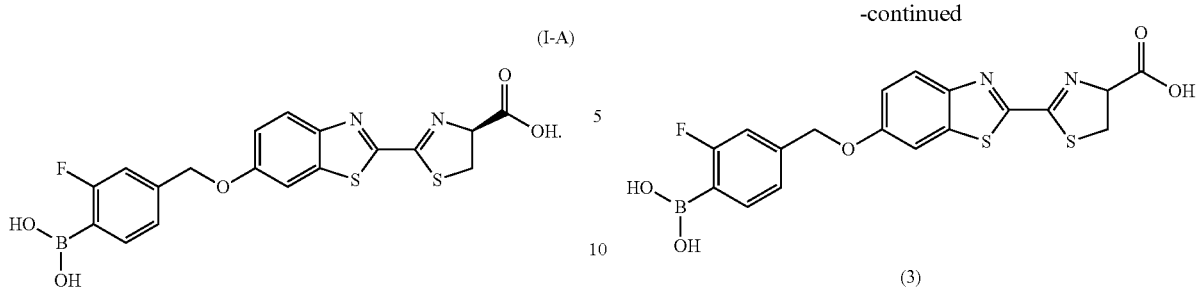

In another embodiment, the compound of formula (I) has the formula (I-B), (I-B)

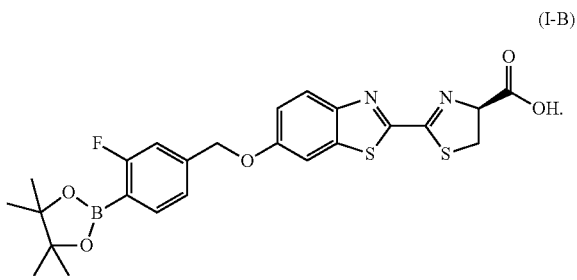 [SMILES: CC1(C)OB(c2ccc(COc3ccc4nc(C5=N[C@@H](C(=O)O)CS5)sc4c3)cc2F)OC1(C)C]

The compounds of the invention contain asymmetric centers and can thus occur as racemates and racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

Synthetic Methods

The compounds and compositions of the invention can be better understood in connection with the following synthetic schemes and methods which illustrate a means by which the compounds can be prepared.

Scheme 1

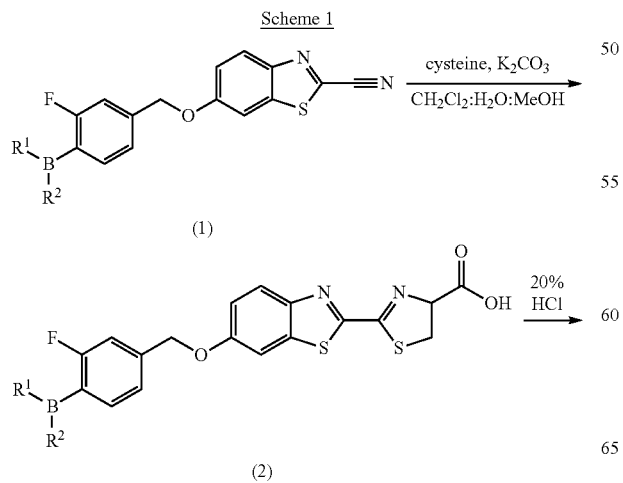

(3)

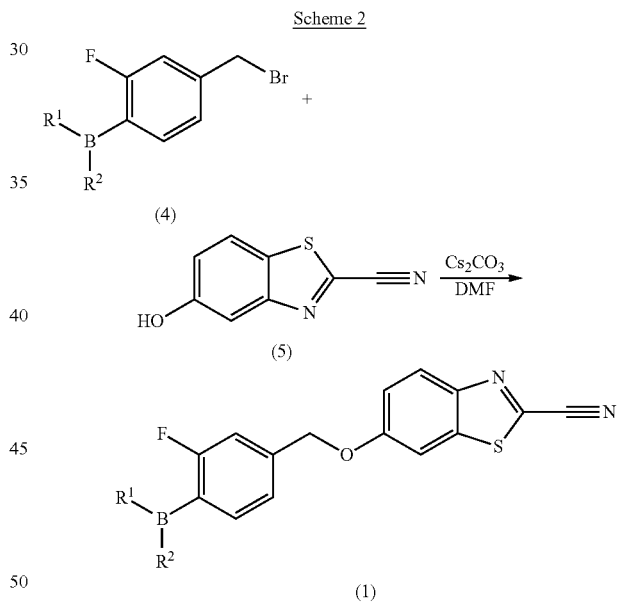

PCL compounds of formula (3) can be prepared as described in Scheme 1. Treatment of the compound of formula (1) with cysteine under anaerobic conditions will provide compounds of formula (2), wherein $R^1$ and $R^2$ are each alkoxy or together with the boron atom to which they are attached form a dioxaborolanyl group. Acidification of the compounds of formula (2) with a strong acid hydrolyzes the boronic ester to a boronic acid, and thereby provides PCL compounds of formula (3). In certain embodiments, the two steps (i.e., dihydrothiazole formation and boronic ester hydrolysis) can be performed sequentially in one pot, thereafter isolating the compounds of formula (3) using known isolation and purification techniques.

Scheme 2

The compounds of formula (1) can be prepared as described in Scheme 2. Compounds of formula (4) can be purchased from Combi-blocks, Inc (San Diego, Calif.). Compounds of formula (4) can be coupled with 2-cyano-6-hydroxybenzothiazole (5) under basic conditions (e.g., $Cs_2CO_3$/DMF) to provide compounds of formula (1), wherein $R^1$ and $R^2$ are each alkoxy or together with the boron atom to which they are attached form a dioxaborolanyl group. The 2-cyano-6-hydroxybenzothiazole compound of formula (5) can be prepared by known methods, such as described in Yao et al., "A Bioluminogenic Substrate for In vivo Imaging of β-Lactamase Activity," *Angew. Chem. Int. Ed.* 2007, 46, 7031-7034; and WO 2011/133800, page 56.

In certain embodiments, the products can be further modified, for example, by manipulation of substituents.

These manipulations can include, but are not limited to, reduction, oxidation, organometallic cross-coupling, alkylation, acylation, and hydrolysis reactions which are commonly known to those skilled in the art. In some cases, the order of carrying out the foregoing reaction schemes can be varied to facilitate the reaction or to avoid unwanted reaction products.

PCL-F for Detecting Peroxynitrite

The compounds of the present invention are useful for detecting peroxynitrite. In one preferred embodiment, a compound useful for detecting peroxynitrite is PCL-F (see Example 2C):

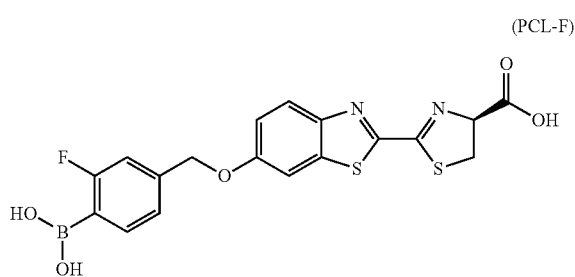 [SMILES: O=C(O)[C@H]1CSC(c2nc3ccc(OCc4ccc(B(O)O)c(F)c4)cc3s2)=N1]

(PCL-F)

PCL-F is a PCL compound of Formula (I), in which $R^1$ and $R^2$ are both hydroxyl, and the stereocenter * is in the (S) configuration.

PCL-F is superior to other known bioluminescent reporter compounds in detecting peroxynitrite. As described in Example 4, PCL-F is resistant to hydrolysis in comparison to PCL-1, and is much more selective than the non-fluorinated peroxy-caged-luciferin PCL-1 in detecting peroxynitrite vs. hydrogen peroxide.

In certain embodiments, the compounds of the invention can be used to detect peroxynitrite in a living cell by contacting a compound of the invention with a living cell in vitro, e.g., a compound of the invention can be contacted with living cells growing in a suspension (e.g., as unicellular entities) or as a monolayer in in vitro cell culture; and detecting a signal generated by reaction of the compound with peroxynitrite in the cell. The cells can be, in non-limiting examples, primary cells, non-transformed cells, cells isolated from an individual, immortalized cell lines, or transformed cells.

Non-limiting examples of cells are cells of multicellular organisms, e.g., cells of invertebrates and vertebrates, such as myoblasts, neutrophils, erythrocytes, osteoblasts, chondrocytes, basophils, eosinophils, adipocytes, invertebrate neurons (e.g., *Helix aspera*), vertebrate neurons, mammalian neurons, adrenomedullary cells, melanocytes, epithelial cells, and endothelial cells; tumor cells of all types (e.g., melanoma, myeloid leukemia, carcinomas of the lung, breast, ovaries, colon, kidney, prostate, pancreas and testes); cardiomyocytes, endothelial cells, lymphocytes (T-cell and B cell), mast cells, vascular intimal cells, hepatocytes, leukocytes including mononuclear leukocytes; stem cells such as hematopoietic stem cells, neural, skin, lung, kidney, liver and myocyte stem cells; osteoclasts, connective tissue cells, keratinocytes, melanocytes, hepatocytes, and kidney cells.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells (CellBank No. JCRB0403), BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), human embryonic kidney (HEK) cells (ATCC No. CRL1573), HLHepG2 cells (ATCC No. HB-8065), and the like.

In certain embodiments, the compounds of the invention can be used to detect peroxynitrite in a living cell in vivo, e.g., in a living multicellular organism. In some embodiments, the method involves administering a compound of the invention (or a composition comprising a compound of the invention) to a multicellular organism (e.g., an individual such as a mammal); and detecting a signal generated by reaction of the compound with peroxynitrite in a cell of the multicellular organism (e.g., in a cell of the individual). These detection methods can also be carried out ex vivo, e.g., where a tissue or cells are taken from an individual and imaged.

The present disclosure also provides methods for detecting peroxynitrite in a multicellular organism, where the peroxynitrite is present extracellularly or intracellularly in the multicellular organism. In some embodiments, the methods involve administering a compound (or a composition comprising a compound of the invention) to a multicellular organism (e.g., an individual such as a mammal); and detecting a signal generated by reaction of the compound with peroxynitrite in the multicellular organism. The peroxynitrite can be present in an extracellular fluid (e.g., cerebrospinal fluid, lymph, plasma, and the like) or other extracellular environment.

Suitable methods of detecting a signal generated by reaction of a compound of the invention with peroxynitrite in a living cell in vitro include, e.g., microscopy, fluorescence activated cell sorting, spectroscopy (e.g., a multi-well plate reader that detects luminescence), luminometers, photomultiplier tubes, and the like. Suitable methods of detecting a signal generated by reaction of a compound of the invention with peroxynitrite in a living cell in vivo include, e.g., use of a charged-coupled device (CCD) camera; a cooled CCD camera; or any other device capable of bioluminescent imaging. Use of a CCD camera can allow three-dimensional imaging of the level of peroxynitrite.

Because peroxynitrite has been implicated in a variety of diseases and conditions, the compounds, compositions, and methods disclosed herein can be used to detect such diseases and conditions in a non-invasive and real-time manner in living tissues or organisms. Non-limiting examples of diseases and conditions, which have been linked to reactive oxygen species, and which can be detected using the compounds, compositions, and methods disclosed herein, include Alzheimer's disease, Parkinson's disease, Huntington's disease, amyotrophic lateral sclerosis, dementia, atherosclerosis, post infarction myocardial complications, arrhythmias, stroke, post-stroke tissue damage, acute respiratory disease syndrome, chronic obstructive pulmonary disease, pulmonary hypertension, vascular hypertension, cancer, ischemia-reperfusion injury, arthritis, inflammatory bowel disease, ulcerative colitis, AIDS, hepatitis, septic shock, chronic rejection of renal grafts, diabetes, gout, pancreatitis, meningitis, influenza, lupus and other autoimmune disorders, inflammation, and radiation-induced gastrointestinal injury, including injury induced by atomic blast radiation and/or medical radiation.

PCL-1 for Detecting Peroxynitrite

In certain embodiments, the invention provides methods of detecting radiation induced gastrointestinal injury in a subject comprising administering to the subject a compound of the formula:

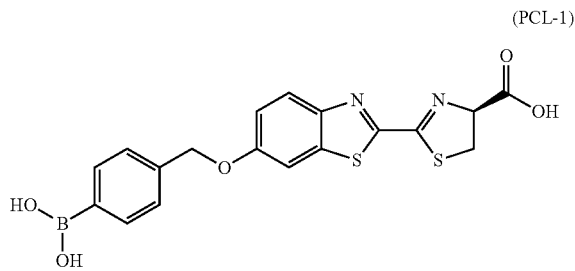 [SMILES: O=C(O)[C@H]1CSC(c2nc3ccc(OCc4ccc(B(O)O)cc4)cc3s2)=N1]

(PCL-1)

and detecting a signal generated by reaction of PCL-1 with peroxynitrite in the feces of the subject. In other embodiments, the invention provides methods of detecting radiation induced gastrointestinal injury in a subject comprising administering to the subject a PCL-F compound.

PCL-1 is a PCL compound with a structure similar to that of PCL-F, except it does not comprise a fluoro substituent on the benzyloxy moiety. As shown in Example 5, PCL-1 is a specific, sensitive, quantitative and versatile biosensor for the detection of peroxynitrite that can permit the elucidation of $NO/O_2^-$ and peroxynitrite roles in health and disease. PCL-1 is insensitive towards NO, superoxide radical anion, HOCl, and singlet oxygen. Among the biologically relevant oxidants the only one that presented appreciable reactivity towards PCL-1 was $H_2O_2$. In the particular case of $H_2O_2$, it was determined that, in vitro and in the absence of GSH, albumin, or catalase, PCL-1 is quantitatively converted to luciferin. Nevertheless, the much higher reactivity of $H_2O_2$ with biological antioxidants present at mM concentrations in cells and in biological fluids precludes any appreciable reaction of PCL-1 with $H_2O_2$. Indeed, it was demonstrated that in the presence of GSH, albumin or catalase, $H_2O_2$-mediated conversion of PCL-1 to luciferin is negligible while none of these compounds affects peroxynitrite reactivity with PCL-1 by more than 10% at the tested concentrations. As shown in Example 5, significant degradation of PCL-1 derived D-Luciferin was not observed over the course of experimentation, even in the absence of added antioxidants.

Compositions

The present invention provides compositions, including pharmaceutical compositions, comprising a compound of the present invention. Compositions comprising a compound of the invention can include one or more of: a salt, e.g., NaCl, MgCl, KCl, $MgSO_4$, etc.; a buffering agent, e.g., a Tris buffer, N-(2-Hydroxyethyl) piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino) propanesulfonic acid (MOPS), N-tris[Hydroxymethyl]methyl-3-aminopropane-sulfonic acid (TAPS), etc.; a solubilizing agent; a detergent, e.g., a non-ionic detergent such as Tween-20, etc.; a membrane penetration facilitator; and the like.

A compound of the invention can be formulated with one or more pharmaceutically acceptable excipients. A wide variety of pharmaceutically acceptable excipients are known in the art, such as described in A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc.

A compound of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. In some case embodiments, a suitable excipient is dimethylsulfoxide (DMSO). In other embodiments, DMSO can be specifically excluded.

For oral preparations, a compound of the present invention can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A compound of the present invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A compound of the present invention can be utilized in aerosol formulation to be administered via inhalation. A compound of the invention can be formulated into pressurized acceptable propellants such as dichlorodifluoromethane, propane, nitrogen and the like.

Furthermore, a compound of the present invention can be made into suppositories by mixing with a variety of bases such as emulsifying bases or water-soluble bases. Such a composition can be administered rectally via a suppository. The suppository can include vehicles such as cocoa butter, carbowaxes and polyethylene glycol monomethyl ethers, which melt at body temperature, yet are solidified at room temperature.

Kits

The present invention provides kits that include one or more bioluminescent reporter compounds of the present invention. The kits can be used for in vitro or in vivo measurement of peroxynitrite. For example, the kits can be used to measure peroxynitrite in cells in the laboratory and/or animals for detection of reactive species in vivo. Optionally, additional oxidants, including reactive oxygen species such as $H_2O_2$, can be measured with a kit of the present invention.

In one embodiment, a kit can include a first vial containing PCL-F and a second vial containing an organic solvent system, an aqueous solvent system, or an aqueous organic solvent system. For example, the solvent system can be dimethylsulfoxide (DMSO) or DMSO-$H_2O$. To measure peroxynitrite, the vials can be combined and the solution or mixture injected into the selected system and the bioluminescence thereafter recorded to measure peroxynitrite in the system. The solution or mixture of bioluminescent reporter compound can be delivered via intravenous injection for example.

In another embodiment, a kit can include a first vial containing PCL-F, a second vial containing PCL-1, and a third vial containing a solvent system, such as an organic solvent system, an aqueous solvent system, or an aqueous organic solvent system. For example, the solvent system can be dimethylsulfoxide (DMSO) or DMSO-$H_2O$. To measure peroxynitrite, the vials can be combined and the solution or mixture delivered into the selected system and the bioluminescence thereafter recorded to measure peroxynitrite in the system. In some embodiments, the kit optionally includes one or more control vials. In some embodiments, the kit optionally includes instructions for using the kit.

In some embodiments, kits of the present invention can include a first vial containing PCL-F, a second vial containing coumarin-7-boronic acid (CBA), and a third vial containing a solvent system, such as an organic solvent system, an aqueous solvent system, or an aqueous organic solvent system. For example, the solvent system can be dimethylsulfoxide (DMSO) or DMSO-$H_2O$. To measure peroxynitrite, the vials can be combined and the solution or mixture delivered into the selected system and the bioluminescence thereafter recorded to measure peroxynitrite in the system. In some embodiments, the kit optionally includes one or more control vials. In some embodiments, the kit optionally includes instructions for using the kit.

Optionally, kits of the present invention can be used to measure the presence of peroxynitrite as well as additional oxidants present in a selected system. For example, in some embodiments, a kit comprising PCL-F and PCL-1 can be used to measure simultaneously both peroxynitrite and $H_2O_2$ by taking advantage of the ablation of $H_2O_2$ reactivity of the PCL-F variant. This kit (in a strip, 96-well plate, laminar flow format, or the like) involves treatment of zones of immobilized or quarantined PCL-1 and PCL-F with a small amount of sample solution, and imaging of bioluminescence after treatment with recombinant luciferase. Concurrent bioluminescence in both PCL-F and PCL-1 containing channels indicates a positive and quantifiable measurement of peroxynitrite—the dynamic range of which is tunable by doping the sensor with reductant (either bovine serum albumin or glutathione). Excess reactivity in a PCL-1 channel vs. a PCL-F channel can be interpreted as signal from hydrogen peroxide, the dynamic range of which is similarly tunable. A strip with a large number of standardized zones will allow for simple reading of estimates for both oxidants in the low micromolar range.

In other embodiments, a kit comprising PCL-F and CBA can be used to measure simultaneously both peroxynitrite and $H_2O_2$ by taking advantage of the ablation of $H_2O_2$ reactivity of the PCL-F variant. This kit (in a strip, 96-well plate, laminar flow format, or the like) involves treatment of zones of immobilized or quarantined CBA and PCL-F with a small amount of sample solution, and imaging of bioluminescence after treatment with recombinant luciferase. In some embodiments, CBA and PCL-F are immobilized or quarantined in the same zone(s) because the reaction products of CBA and PCL-F with oxidants are detected at different wavelengths. Concurrent bioluminescence in both PCL-F and CBA containing channels indicates a positive and quantifiable measurement of peroxynitrite—the dynamic range of which is tunable by doping the sensor with reductant (either bovine serum albumin or glutathione). Excess reactivity in a CBA channel vs. a PCL-F channel can be interpreted as signal from hydrogen peroxide, the dynamic range of which is similarly tunable. A strip with a large number of standardized zones will allow for simple reading of estimates for both oxidants in the low micromolar range.

The compounds, compositions, methods and processes of the invention will be better understood by reference to the following examples, which are intended as an illustration of and not a limitation upon the scope of the invention.

Specific embodiments of the present invention include compounds disclosed in the Examples provided herein, and the pharmaceutically acceptable salt, ester, amide, prodrug, and radiolabeled forms thereof.

EXAMPLES

Example 1

Materials and Methods

All reagents were purchased from Sigma Aldrich (St. Louis, Mo.) or ACROS Organics (part of Thermo Fisher, New Jersey, US) unless otherwise stated. Recombinant luciferase was purchased from Promega (Madison, Wis.). UV-vis spectra, kinetic data, and bioluminescence data were obtained using a Spectramax M5 spectrophotometer from Molecular Devices (Sunnyvale, Calif.). PCL-1 was synthesized according to known methods (Van de Bittner et al., 2010, *Proc. Natl. Acad. Sci. USA* 107: 21316-21321), freeze-dried, and stored in aliquots in DMSO at −80° C. protected from light. D-Luciferin was quantified at pH 12 by UV-vis ($\epsilon_{385}$=18200 $M^{-1}$ $cm^{-1}$). Hydrogen peroxide solutions were prepared in Millipore water (18.2 MOhm) from a 33% stock solution, and quantified prior to use via UV-vis ($\epsilon_{240}$=43.6 $M^{-1}$ $cm^{-1}$). Sodium peroxynitrite was generated using a quenched-flow reactor according to known methods (K. M. Robinson et al., "Synthesis of Peroxynitrite from Nitrite and Hydrogen Peroxide," In: *Methods in Enzymology*, 2005, 396:207-214). Peroxynitrite solutions in 10 M NaOH were stored over $MnO_2$ at −80° C. for up to 1 month prior to thaw on ice and quantification by UV-vis ($\epsilon_{302}$=1670 $M^{-1}$ $cm^{-1}$). Solutions of peroxynitrite in 1.0 mM NaOH were added directly to buffered reaction mixtures.

$^1H$ nuclear magnetic resonance (NMR) and $^{13}C$ NMR spectra were determined using a Bruker 360 MHz FT NMR spectrometer. The chemical shifts (6) are expressed in parts per million (ppm) relative to tetramethylsilane (TMS) as the internal standard. Splitting patterns are as follows: s, single; d, doublet; br, broad; m, multiplet. Electrospray mass spectra were determined in positive ion mode using a Shimadzu LCMS IT-TOF mass spectrometer.

Kinetics of peroxynitrite reactivity with PCL-1 was measured with stopped flow absorption spectroscopy. Stopped flow experiments were performed at 22° C. on an Applied Photophysics SX20 stopped flow spectrometer equipped with a Hamamatsu R928 photomultiplier tube. In each experiment 75 µL of PCL-1 (5-100 µM in TBS, pH 7.4) was mixed an equal volume of peroxynitrite (1.0 mM in 1.0 mM NaOH), and absorbance was monitored over the course of 1, 5, or 20 seconds. The slit width was 1 nm, and the path length was 1.0 cm. The time resolution for 1-second experiments was 1 msec. It was necessary to subtract the spectral contribution from excess and consumed peroxynitrite ($\epsilon_{320}=1350$ $M^{-1}$ $cm^{-1}$) before traces were fit to a single exponential curve, and the observed rate was calculated. A plot of PCL-1 concentration vs. observed rate gave a line with slope equal to $k_{ONOO^-}$ for PCL-1.

D-Luciferin formation was quantified by addition of recombinant luciferase to the reaction mixture in a white opaque 96-well plate. To a solution of 200 μL PCL-1 (5 μM) in TBS buffer with 5% DMSO (pH 7.4) was added 100 μL of a solution of recombinant luciferase (100 μg/mL) in 10 mM $MgCl_2$ and 2 mM ATP. After mechanical shaking for 5 seconds, bioluminescence was measured at 612 nm in 30-second increments (100 msec integration time) over 30 minutes. The area under the curve was proportional to the D-Luciferin concentration, and was defined as the photon flux (relative luminescence units (RLU)*sec).

Limit of detection (LOD) was determined according to a 3σ corresponding to a 99% confidence interval. Twenty "blank" wells were prepared by addition 200 μL of 5 μM PCL-1 in 5% DMSO in TBS (pH 7.4) to wells of a white opaque 96-well plate. 20 "sample" wells were prepared by addition of a small amount of analyte (2-10 times the signal from the blank) to the same solution. These concentrations corresponded to 50 nM peroxynitrite, 1 μM for SIN-1, and 250 μM for $H_2O_2$. The 20 wells were treated with 100 μL of 100 μg/mL recombinant luciferase in 100 mM sodium phosphate containing 10 mM $MgCl_2$ and 2 mM ATP, pH 7.4, and bioluminescence was measured at 612 nm every 30 seconds (100 msec integration time) over 30 minutes. Limit of detection was determined following the equation:

$$c_L = k s_{bl} S$$

where $c_L$ is the limit of detection, k is the desired confidence interval, $s_{bl}$ is the standard deviation of the blank measurements, and S is the sensitivity. Limit of quantification (LOQ) was defined as 10 times standard deviation of the 20 blank measurements.

Bone marrow derived macrophages were prepared using 10% L929 cell (ATCC) supernatant in RPMI medium (Cellgro) made complete with 10% FBS, penicillin, streptomycin, and glutamine (Gibco). Cells were cultured 4-6 days prior to plating for experiments in opaque, white microtiter plates (Falcon) for analysis on a Wallac Victor2 luminometer (PerkinElmer).

Example 2

(S)-2-(6-(4-borono-3-fluorobenzyloxy)benzo[d]thiazol-2-yl)-4,5-dihydrothiazole-4-carboxylic acid (also referred to herein as PCL-F)

Example 2A 2-(4-(bromomethyl)-2-fluorophenyl)-4,4,5,5-tetramethyl-1,3,2-dioxaborolane

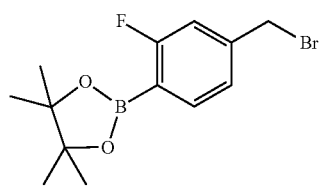 [SMILES: CC1(C)OB(c2ccc(CBr)cc2F)OC1(C)C]

2-(4-(bromomethyl)-2-fluorophenyl)-4,4,5,5-tetramethyl-1,3,2-dioxaborolane was purchased from Combi-Blocks, Inc. (San Diego, Calif.).

Example 2B 6-(3-fluoro-4-(4,4,5,5-tetramethyl-1,3,2-dioxaborolan-2-yl)benzyloxy)benzo[d]thiazole-2-carbonitrile

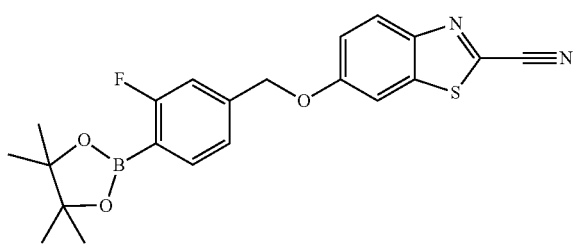 [SMILES: CC1(C)OB(c2ccc(COc3ccc4nc(C#N)sc4c3)cc2F)OC1(C)C]

Example 2A (356.0 mg, 1.13 mmol) and 2-cyano-6-hydroxybenzothiazole (200.4 mg, 1.13 mmol) were dissolved in 20 mL dry DMF prior to the addition of cesium chloride (406.4 mg, 1.25 mmol). The mixture was stirred at 60° C. for 45-50 minutes before it was allowed to cool to room temperature. 50 mL ethyl acetate was added to the reaction, and the organic phase was washed three times with deionized water. The aqueous layers were combined and washed three times with ethyl acetate. All of the organic layers were combined, washed twice with brine, dried over sodium sulfate, and concentrated. The crude material was purified on a silica column (90:10 hexanes:ethyl acetate, dry loaded) to give 320 mg (69%) of the pure product. $^1$H NMR (CDCl$_3$): δ 1.37 (s, 12H), 5.19 (s, 2H), 7.14 (d, J=9.9 Hz, 1H), 7.21 (d, J=7.7 Hz, 1H), 7.31 (dd, J=9.1 Hz, 2.5 Hz, 1H), 7.37 (d, J=2.4 Hz, 1H), 7.78 (t, J=7.3 Hz, 1H), 8.10 (d, J=9.1 Hz, 1H).

Example 2C (S)-2-(6-(4-borono-3-fluorobenzyloxy)benzo[d]thiazol-2-yl)-4,5-dihydrothiazole-4-carboxylic acid (also referred to herein as PCL-F)

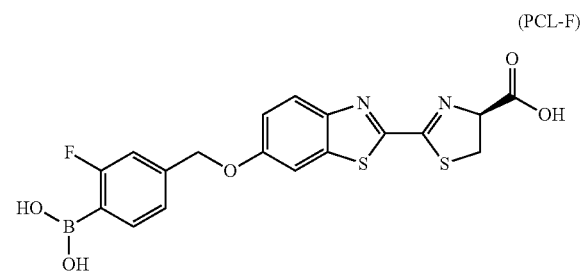 [SMILES: O=C(O)[C@H]1CSC(c2nc3ccc(OCc4ccc(B(O)O)c(F)c4)cc3s2)=N1]

(PCL-F)

D-cysteine hydrochloride (58.7 mg, 0.334 mmol) and potassium carbonate (50.4 mg, 0.364 mmol) were dissolved in 2.0 mL $N_2$-sparged deionized $H_2O$ under an $N_2$ atmosphere. 5.0 mL $N_2$-sparged dichloromethane was added to the flask, followed by the compound of Example 2B (125.0 mg, 0.304 mmol). After the compound of Example 2B dissolved, the flask was charged with 8.0 mL $N_2$-sparged methanol. The flask was monitored to ensure that no precipitate formed while the methanol was added. The reaction was stirred vigorously for ten minutes before 3.0 mL N$_2$-sparged deionized H$_2$O was added to the flask. The dichloromethane and methanol were removed from the flask under low pressure prior to the addition of 25 mL of a N$_2$-sparged 20% aqueous HCl solution. A yellow precipitate formed immediately upon addition of the HCl solution. The mixture was stirred for 15-20 minutes and the precipitate was filtered and washed with deionized H$_2$O until the pH became neutral. The crude material was purified using HPLC (H$_2$O:MeOH, 40-100% MeOH over 45 minutes) to give 35.0 mg (27%) pure product of Example 2C (i.e., PCL-F).

$^1$H NMR (CD$_3$OD): δ 3.35 (s, 1H), 3.77 (br, 2H), 5.22 (s, 2H), 5.37 (br, 1H), 7.21 (d, J=9.5 Hz, 1H), 7.28 (dd, J=9.8 Hz, J=2.4 Hz, 2H), 7.31 (s, 1H), 7.44 (t, J=7.0 Hz, 1H), 7.64 (m, 1H), 7.99 (d, J=9.0 Hz, 1H). $^{13}$C NMR (CD$_3$OD): δ 159.7, 135.6, 125.9, 124.0, 118.7, 114.8, 114.5, 106.4, 85.7, 79.8, 70.6, 36.0, 2.3. Electrospray ion mass spectroscopy (positive ion mode) for the compound of Example 2C yielded a m/z of 433.0478 (calculated: 433.2659) for PCL-F, and a m/z of 415.0563 (calculated: 415.2748) for the non-fluorinated peroxy-caged-luciferin (PCL-1).

Example 3

Electronic Absorption Spectrum

Figures 9A, 9B:
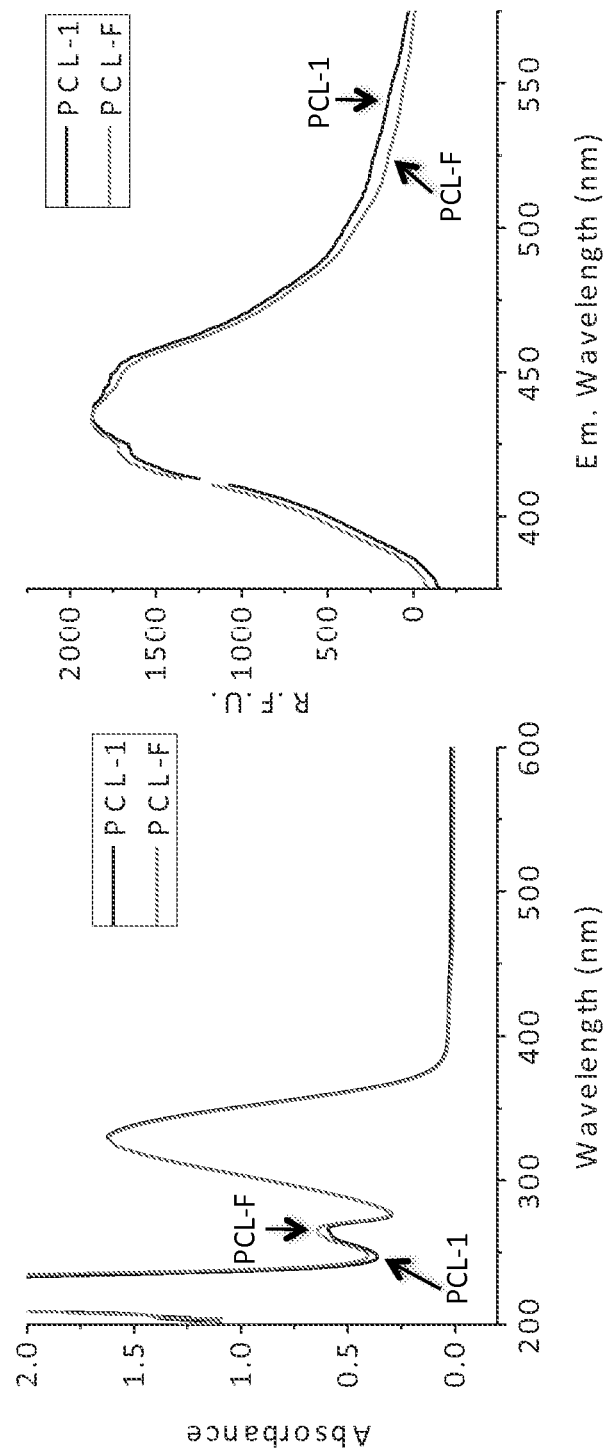
FIG. 9A shows absorbance spectra of PCL-1 and PCL-F.
FIG. 9B shows fluorescence emission spectra of PCL-1 and PCL-F.

FIG. 9A shows an electronic absorption spectrum of an 80 μM solution of the compound of Example 2C (PCL-F) in PBS at a pH of 7.4, as compared to the non-fluorinated peroxy-caged-luciferin (PCL-1).

Example 4

Bioluminescence

FIG. 1 shows plots of total bioluminescence upon treatment of PCL-1 or PCL-F (5 μM) with a minimal amount of SIN-1 (2.5 μM) or H$_2$O$_2$ (25 μM) for 60 minutes at 37° C. Recombinant luciferase was added to the reaction mixture and bioluminescence was detected at 612 nm for 60 minutes. D-Luciferin (5 μM) was used as a determinant of maximum yield. FIG. 1 demonstrates that PCL-F is resistant to hydrolysis in comparison to PCL-1, and when subject to trace amounts of oxidant, and is more selective than PCL-1 in detecting peroxynitrite vs. hydrogen peroxide.

Figures 2A, 2B:
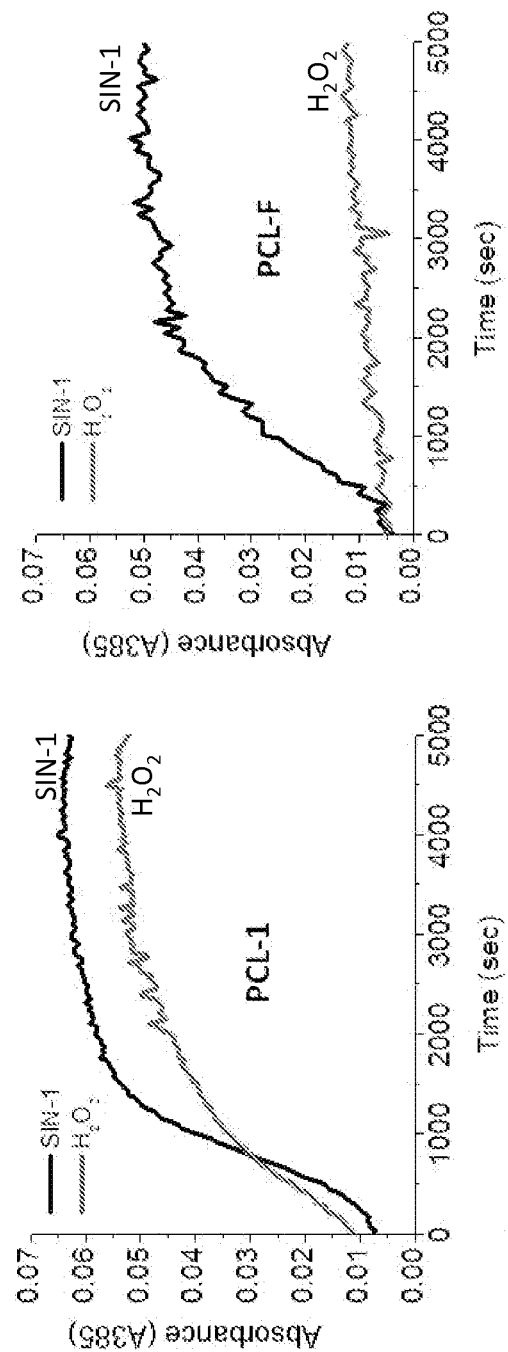
FIGS. 2A and 2B show kinetic plots of formation of D-Luciferin upon treatment of PCL-1 (FIG. 2A) or PCL-F (FIG. 2B) with 100 µM 3-morpholinosydnonimine (SIN-1, which generates peroxynitrite) or $H_2O_2$.
Figure 2D:
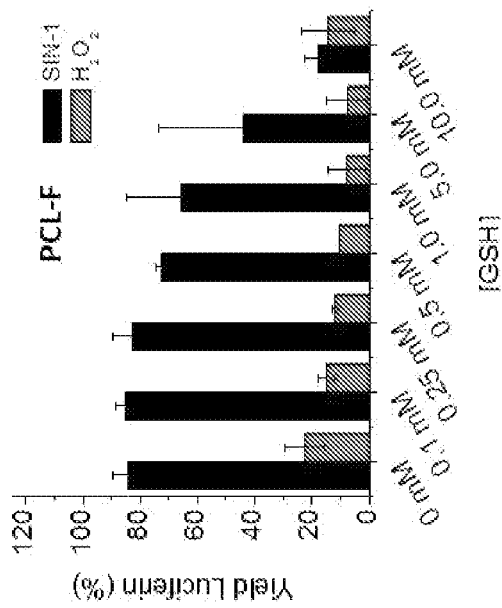
FIGS. 2C and 2D show the maximum yield of D-Luciferin obtained upon treatment of 5 µM PCL-1 or PCL-F, respectively, with 100 µM SIN-1 or $H_2O_2$ in the presence of increasing concentrations of glutathione.
Figure 2C:
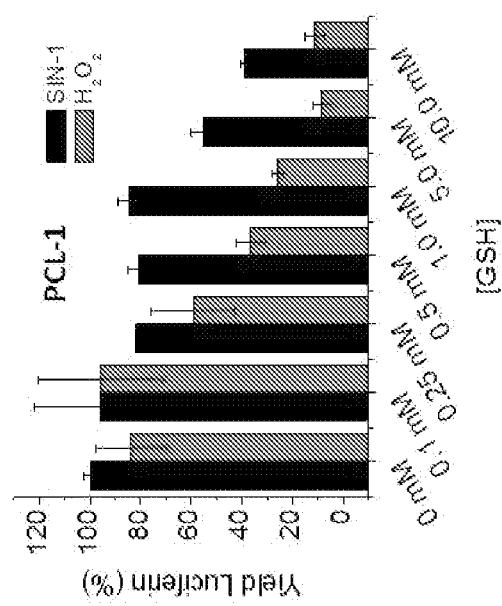

FIG. 2 shows kinetic plots of formation of D-Luciferin (measured by absorbance at 385 nm) upon treatment of 5 μM PCL-1 (FIG. 2A) or PCL-F (FIG. 2B) in TBS, pH 8.5, at 37° C. with 100 μM SIN-1 or H$_2$O$_2$ over the course of 90 minutes. FIGS. 2C and 2D show the maximum yield of D-Luciferin obtained upon treatment of 5 μM PCL-1 or PCL-F, respectively, with 100 μM SIN-1 or H$_2$O$_2$ in the presence of increasing concentrations of glutathione (a competing scavenger of peroxynitrite) over the course of 90 minutes. Little reactivity with H$_2$O$_2$ was observed with PCL-F compared to PCL-1. In addition, reactivity of PCL-F with SIN-1 was retained until concentrations of 1-5 mM glutathione were used. These data demonstrate remarkable selectivity improvement in PCL-F over PCL-1 in detection of peroxynitrite over hydrogen peroxide, as well as fast enough reactivity to achieve significant conversion to D-Luciferin in the presence of milieu competition such as active thiols. While it was expected that a decrease in overall reactivity would be observed in PCL-F over PCL-1, it was surprising that introduction of an electron-withdrawing fluorine atom in the aryl ring of the boronic acid resulted in a compound with ablated reactivity with hydrogen peroxide, yet still detected peroxynitrite in the presence of biologically relevant amounts of competing thiols (glutathione).

Example 5

Figures 3A, 3B:
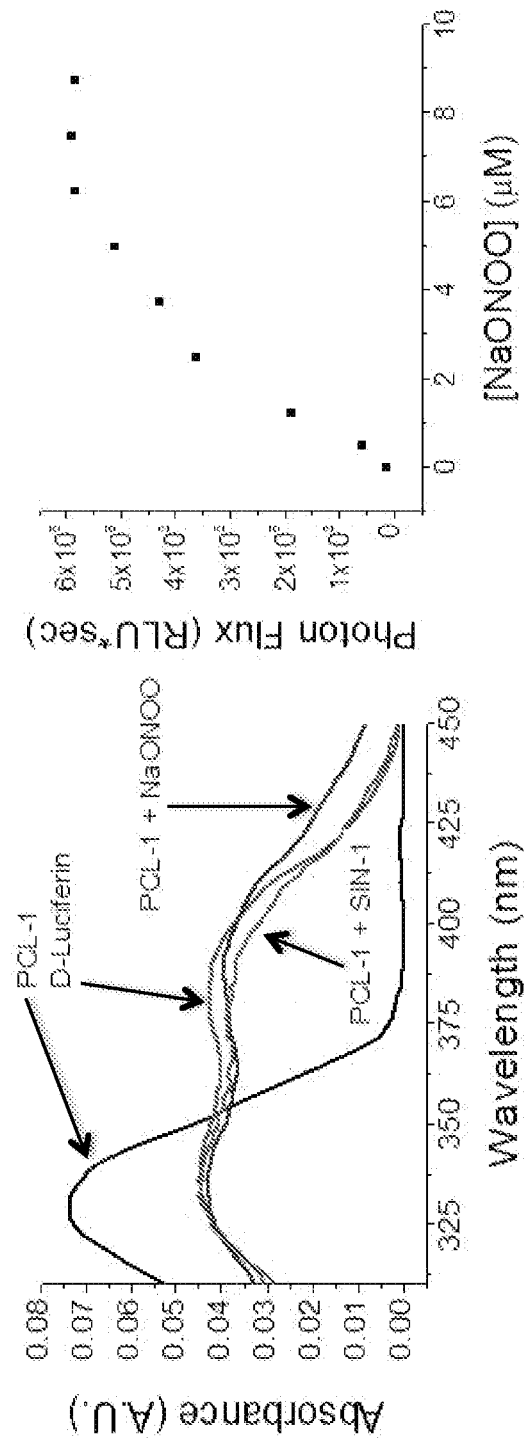
FIG. 3A shows an electronic absorbance spectrum of PCL-1.
FIGS. 3B-3D show kinetics profiles of PCL-1 in detecting peroxynitrite.

PCL-1 Reacts Rapidly with Peroxynitrite and Converts Stoichiometrically to D-Luciferin FIG. 3A shows an electronic absorption spectrum of D-Luciferin (5 μM) and PCL-1 (5 μM) in TBS (pH 8.5) along with treatment of PCL-1 with either bolus peroxynitrite (10 μM) or in-situ generated peroxynitrite from combination of NO and O$_2^-$ from 100 μM 3-morpholinosydnonimine (SIN-1) for 60 minutes at 37° C. Where applicable, spectral contributions from oxidants were subtracted via a parallel blank experiment containing no PCL-1. As shown in FIG. 3A, this resulted in an electronic absorption spectrum which overlays with that of authentic D-Luciferin.

To confirm formation of D-Luciferin, recombinant luciferase was added to the reaction mixture and bioluminescence was recorded as described in Example 1. Peak bioluminescence was observed treatment of approximately 5 μM PCL-1 in TBS (pH 7.4) with increasing peroxynitrite for 30 minutes and subsequent addition of recombinant luciferase. Results are shown in FIG. 3B as a plot of photon flux vs. peroxynitrite concentration. With a bioluminescent output, a detection limit was calculated of 16 nM for peroxynitrite after incubation at 37° C. for 30 minutes, compared to that of 231 nM with hydrogen peroxide (Table 1).

Figures 3C, 3D:
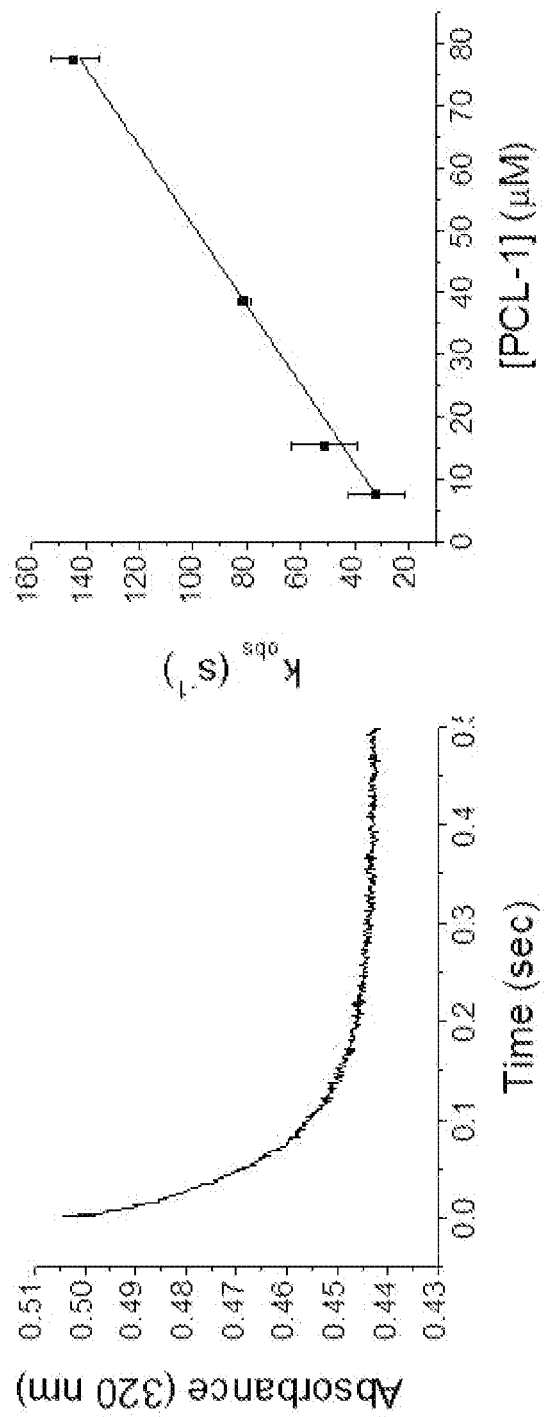

To obtain the rate constant for PCL-1 with peroxynitrite, the decay of PCL-1 was monitored using stopped-flow spectroscopy under pseudo first-order conditions (excess peroxynitrite). Stopped-flow kinetics were measured upon rapid mixing of PCL-1 (155 μM) in TBS, pH 7.4 with Peroxynitrite (1.0 mM) in NaOH (1.0 mM) at 21° C. Results are shown in FIG. 3C.

A plot of the dependence of the observed initial rate on PCL-1 concentration (FIG. 3D) was used to determine $k_{ONOO^-}$ for PCL-1. As shown in Table 1, this corresponds to roughly 1-million fold faster reactivity than hydrogen peroxide. The rate constant observed with SIN-1-derived peroxynitrite was consistent with the slower decomposition of SIN-1 to generate peroxynitrite being the rate limiting step.

TABLE 1

Detector Parameters for Peroxy-Caged-Luciferin-1 (PCL-1)

| Oxidant | Maximum Yield Luciferin(%)* | Rate ($M^{-1}sec^{-1}$) | L.O.D. (nM)** | L.O.Q. (nM)*** |
|---|---|---|---|---|
| H$_2$O$_2$ | 97 | 1.2 ± (0.3) | 231 | 763 |
| Peroxynitrite (bolus) | 95 | 9.8 ± (0.3) × 10$^5$ | 16 | 56 |
| Peroxynitrite (SIN-1) | 96 | — | 47 | 157 |

*Yield quantified using A$_{385}$, normalized to authentic D-luciferin. Yield corresponds to addition of H$_2$O$_2$ (100 μM), peroxynitrite (10 μM), or SIN-1 (100 μM) to 5 μM PCL-1 in TBS, pH 8.5, at 37° C. and monitoring over 90 minutes.
**Limit of detection, as defined in Example 1.
***Limit of quantification, as defined in Example 1.

Figures 4A, 4B:
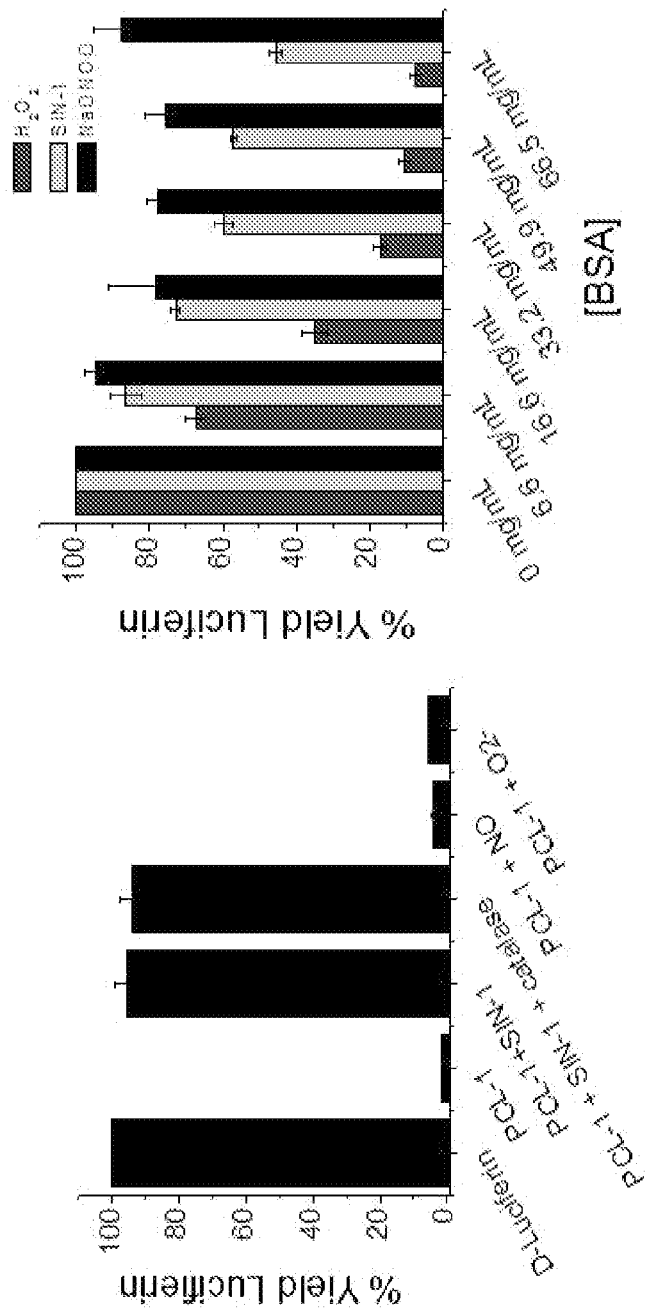
FIGS. 4A-4D show the selectivity of PCL-1 for peroxynitrite.

Addition of glutathione or albumin ablates hydrogen peroxide, but not peroxynitrite detection by PCL-1 in vitro. The environment inside most cellular compartments is "reducing"—a status heavily dependent on the multiple antioxidant systems that rapidly detoxify oxidants in cells such as thioredoxins and glutathione/glutathione reductase redox systems and catalase. A viable biosensor for an oxidant inside of cells and tissue should detect its target in the presence of these and other ubiquitous milieu components. The yield of D-Luciferin from PCL-1 was measured in the presence of $H_2O_2$, and peroxynitrite derived from SIN-1, each in the presence of increasing amounts of glutathione ($k_{ONOO-}$=1.4×10$^3$ M$^{-1}$ sec$^{-1}$) and bovine serum albumin ($k_{ONOO-}$=8.31×10$^3$ M$^{-1}$ sec$^{-1}$). In the case of BSA, a dose dependent decrease in D-Luciferin yield was observed even with added BSA when hydrogen peroxide was used as the oxidant, resulting in only 7.38±1.39% yield luciferin. In stark contrast, 87.5±7.48% yield of D-Luciferin was detected even in the presence of 66.5 mg/mL BSA (1.0 mM) (FIG. 4B). In the case of SIN-1, 45.49% D-luciferin was obtained. This can be due to NO scavenging by the BSA non-polar core, which prevents NO from reacting with the hydrophilic superoxide ion.

Example 6

Figures 4C, 4D:
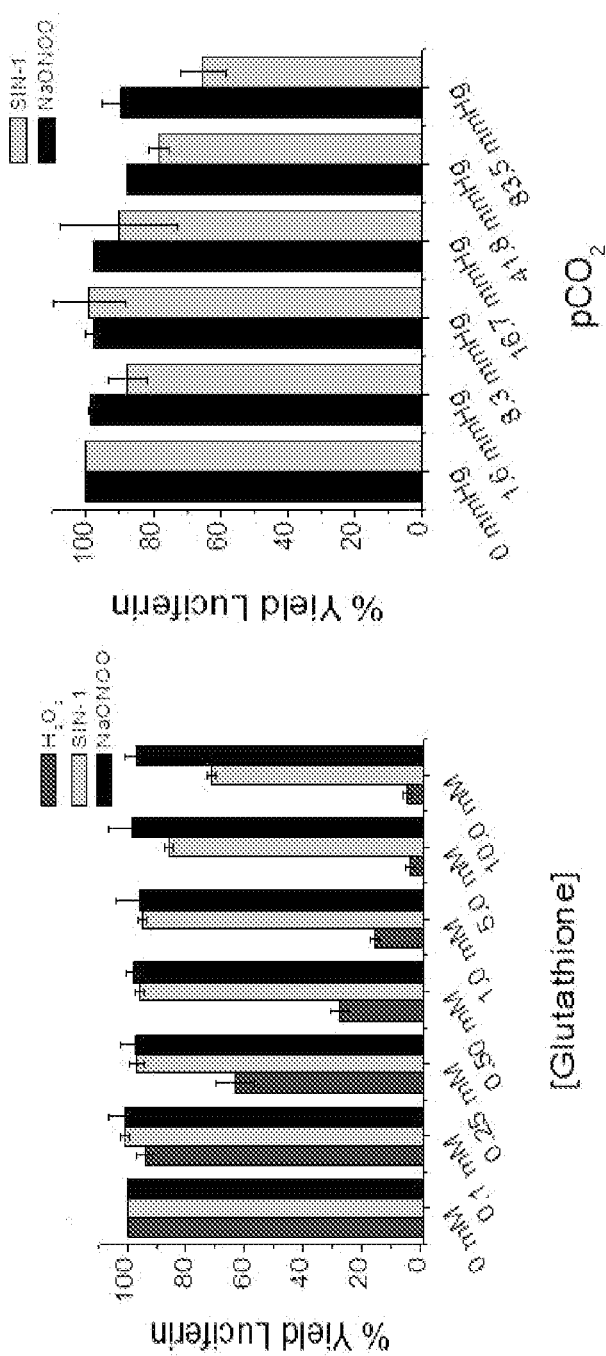

PCL-1 Detects Peroxynitrite Selectively and in the Presence of Milieu Components FIG. 4A shows a plot of yield of D-Luciferin after treatment of PCL-1 (5 μM) in TBS with SIN-1 (100 μM), catalase (500 μg/mL), NO (66 mM DEANO), or $O_2^-$ (100 μM KO$_2$) for 90 minutes, and subsequent addition of recombinant luciferase to the reaction mixture according to Example 1. Data were normalized to bioluminescence obtained from an identical treatment of authentic D-Luciferin (5 μM). FIGS. 4B-4D show plots of total D-Luciferin obtained ($A_{385}$) from treatment of 5 μM PCL-1 with either $H_2O_2$ (200 μM), SIN-1 (100 μM), or peroxynitrite (10 μM) for 90 minutes in the presence of increasing concentrations of BSA, glutathione, and $CO_2$, respectively. In all cases, spectral contributions from oxidants were subtracted via a parallel blank experiment containing no PCL-1.

Example 7

Detection of iNOS-Derived Peroxynitrite in Mouse Bone Marrow Derived Macrophages In order to validate the utility of PCL-1 to detect peroxynitrite in cells, mouse bone marrow-derived macrophages (BMDM) were stimulated with 50 ng/mL bacterial LPS (lipopolysaccharide) for 22 hours, 5 μM PCL-1 was added for an additional 2 hours, then D-Luciferin generated was quantified over the course of 2 hours by addition of 100 mg/mL recombinant luciferase, according to Example 1.

Figure 5:
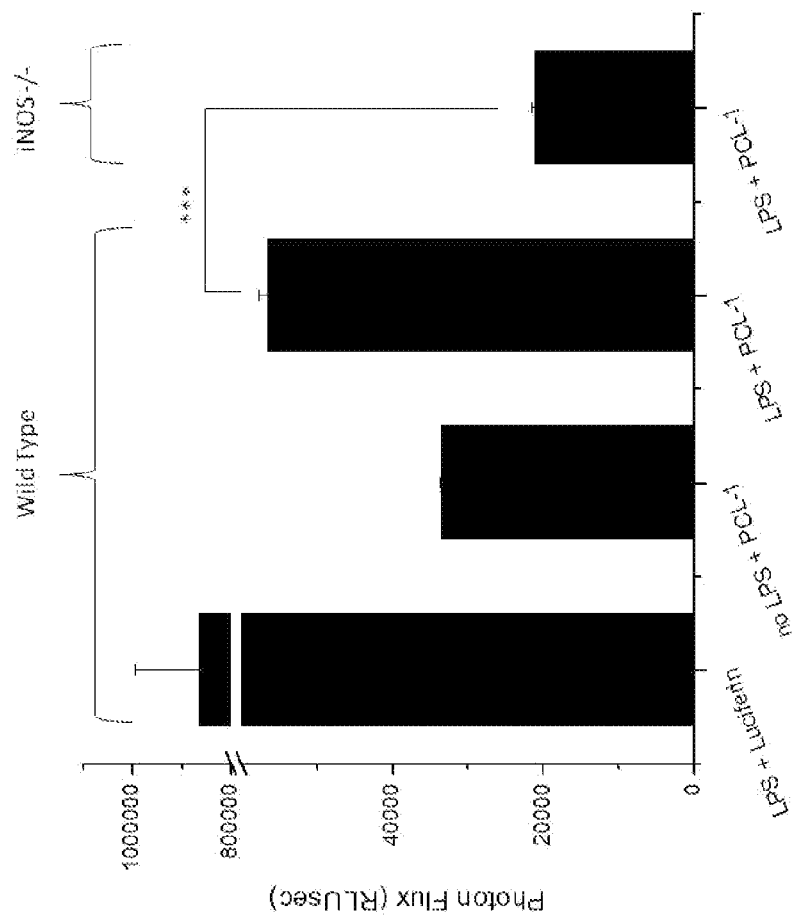
FIG. 5 shows a plot of bioluminescence photon flux of bone-marrow derived macrophages (BMDM) with and without lipopolysaccharide (LPS) (50 ng/mL) and PCL-1, including BMDMs from iNOS$^{-/-}$ animals. BMDMs were treated for 22 hours and quantification of bioluminescence took place over 2 hours.

As shown in FIG. 5, a nearly two-fold increase of D-Luciferin production was observed over the baseline value after stimulation of wild-type macrophages with LPS for 24 hours. Importantly, using BMDMs from iNOS$^{-/-}$ animals resulted in no signal above baseline, showing that the species contributing to D-Luciferin production was produced in a NOS-dependent manner. This demonstrates detection of peroxynitrite in a cellular system not activated to simultaneously produce NO and $O_2^-$. This observation demonstrates the superiority of PCL compounds over other methodologies to detect peroxynitrite that require a double hit type of stimulation to maximize the concentration of the oxidant. It also shows that PCLs can detect peroxynitrite production even in the presence of excess NO.

Example 8

Irradiated Mouse Model

Figure 6:
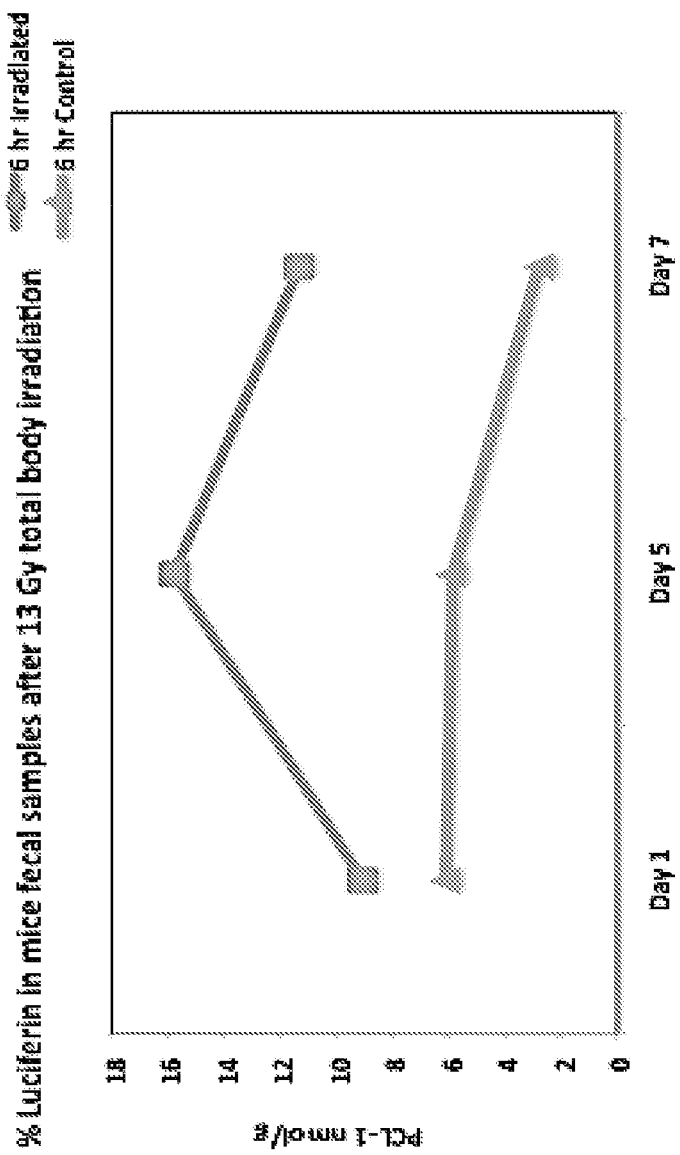
FIG. 6 shows percent luciferin detected in mice fecal samples at days 1, 5 and 7 in control and irradiated (13 Gy) mice fecal samples.
Figure 7A:
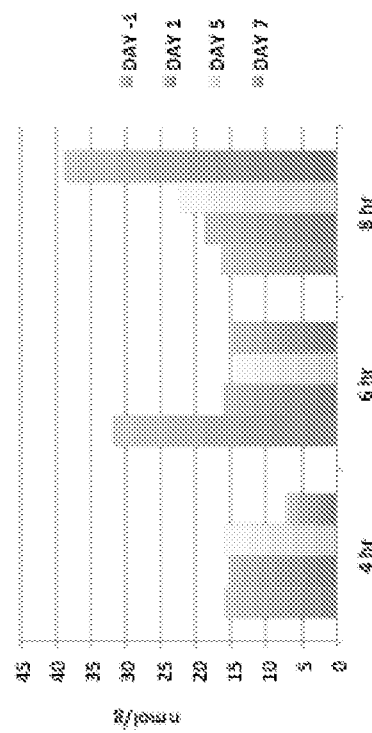
FIG. 7 shows PCL-1 levels in mice fecal samples at baseline and at days 1, 5 and 7 in irradiated (FIG. 7B) and control non-irradiated (FIG. 7A) mice. For each time point (4 hr, 6 hr, or 8 hr), the four histogram bars correspond to Day −1, Day 1, Day 5, and Day 7, from left to right.
Figure 7B:
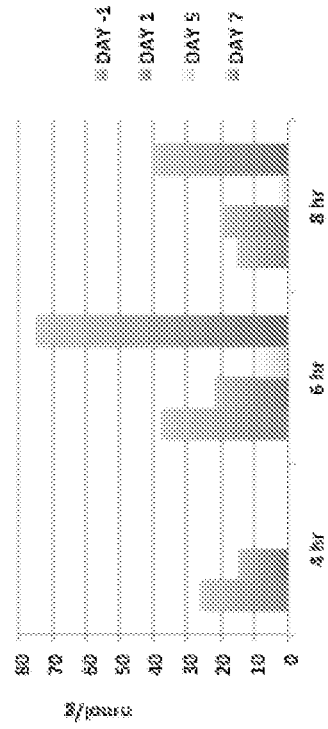

C57BL/6 mice were irradiated at a high lethal dose of 13Gy or at a LD$_{70/30}$ of 8.1Gy in independent experiments using a Cs$^{137}$ source. PCL-1 was administered via oral gavage at 40 or 60 μM/animal, 0.2 mL volume per animal. Fecal samples were collected from the orbital sinus bleeding from the irradiated and non-irradiated mice at different time points (pre-dose, 4, 6 and 8 hr post-dose) prior to irradiation and also on days 1, 5 and 7 post-irradiation from all animals. PCL-1 and cleaved PCL-1 (luciferin) levels were measured in the feces using LC-MS/MS method. In the 13 Gy irradiation study significant increase of about 3 fold in the level of the marker was noted in the fecal samples collected between days 5 to 7 in mice irradiated at 13Gy as compared to the control levels with $C_{max}$ at about 6 hrs post dose (FIG. 6).

Figure 8A:
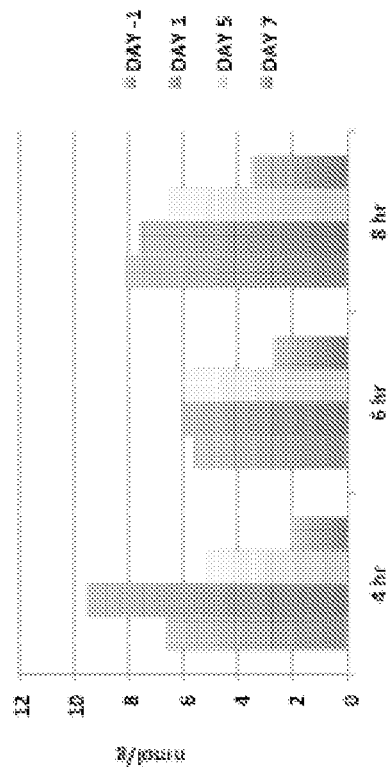
FIG. 8 shows the percent luciferin trend in mice fecal samples at baseline and at days 1, 5 and 7 in irradiated (FIG. 8B) and control non-irradiated (FIG. 8A) mice. For each time point (4 hr, 6 hr, or 8 hr), the four histogram bars correspond to Day −1, Day 1, Day 5, and Day 7, from left to right.
Figure 8B:
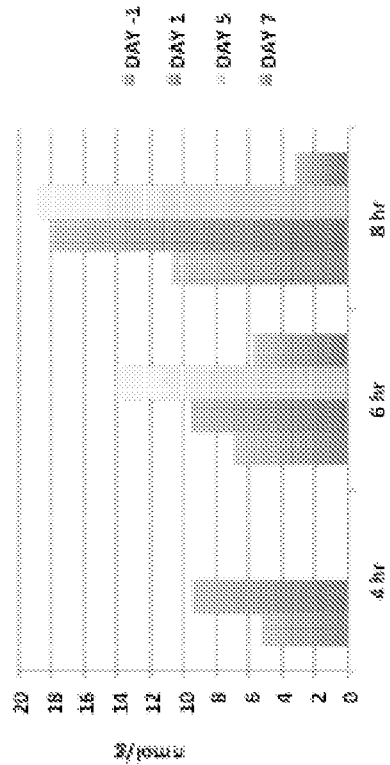

In the case of 8.1Gy irradiation, a two-fold or more increase in PCL-1 and % cleaved PCL-1 levels was seen in the feces until day 7 (FIGS. 8 and 9). It was also observed that, post irradiation, the appearance of the fecal marker was moved to later time points probably due to decreased GI motility.

To confirm the safety of PCL-1 in mice, it was administered between 40 to 250 μM per animal via oral gavage and no signs of toxicity were observed.

Additionally with up to a 6.25 fold increase in dose a directly proportional fold increase in marker detected was not observed. Hence a lower dose of PCL-1 could be used to provide relevant fecal detection, which was not dose dependent (Table 2).

TABLE 2

Maximum fecal concentrations (Cmax) of PCL-1 and luciferin after oral administration of varying concentrations of PCL-1.

| PCL-1 Dose μM/animal | Fold increase in dose | Cmax PCL-1 | LUC | % LUC |
|---|---|---|---|---|
| 40 | — | 24.41 | 1.41 | 5.79 |
| 60 | 1.5 | 31.91 | 1.83 | 8.15 |
| 100 | 2.5 | 14.84 | 0.60 | 4.04 |
| 250 | 6.25 | 25.51 | 1.82 | 7.90 |

Example 9

Spectrophotometric, Fluorometric, and Kinetic Characterization of PCL-F Compared to PCL-1

FIG. 9A shows the absorbance spectra of PCL-1 and PCL-F, obtained in 100 mM sodium phosphate buffer at pH 7.4 containing 5% DMSO.

Figures 9C, 9D:
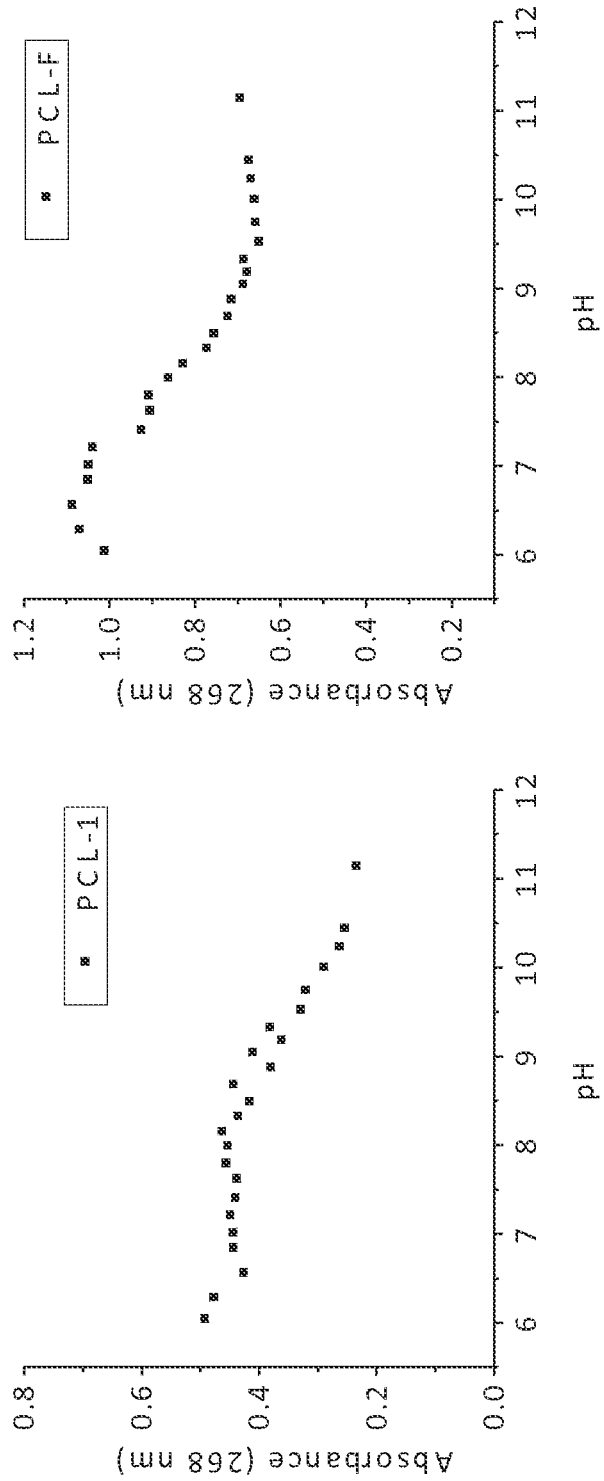
FIG. 9C shows absorbance at 268 nm with varying pH for PCL-1.
FIG. 9D shows absorbance at 268 nm with varying pH for PCL-F.
Figures 10A, 10B:
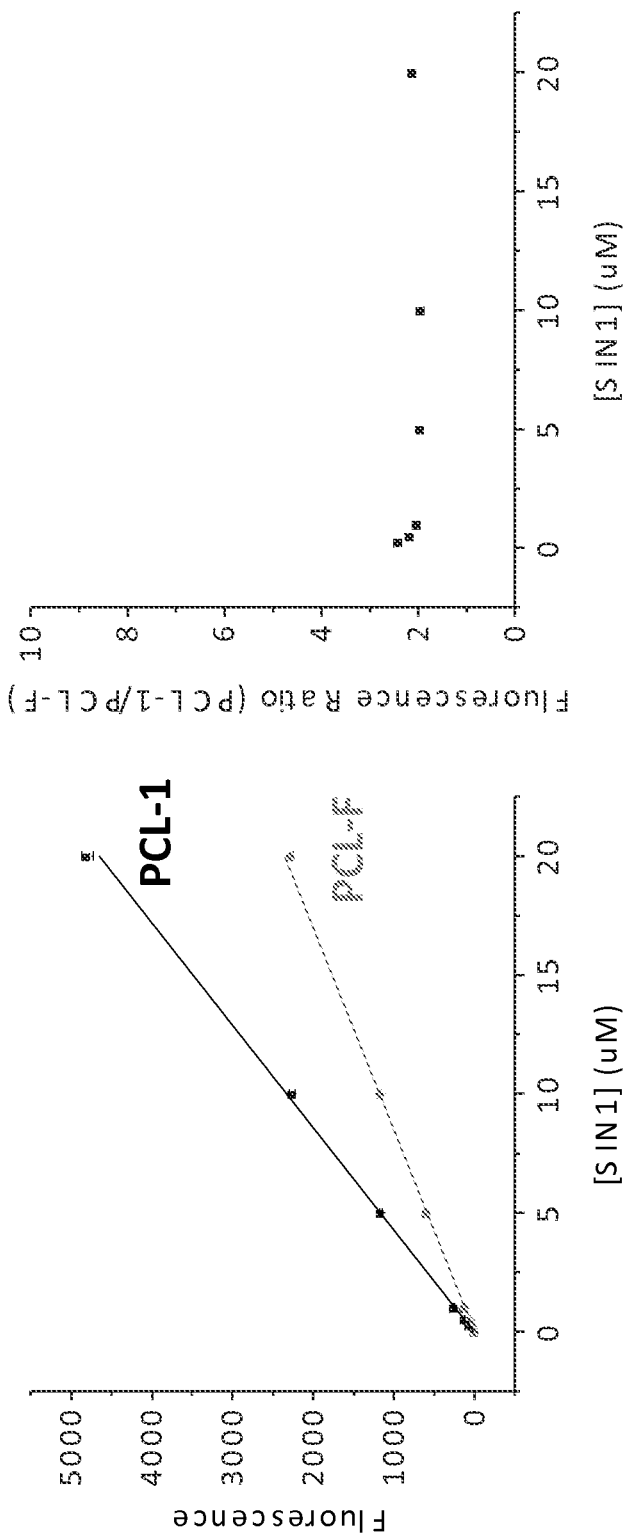
FIG. 10A shows fluorescence of PCL-1 and PCL-F exposed to varying concentrations of SIN-1 and FIG. 10B shows the fluorescence ratio, PCL-1/PCL-F, at varying concentrations of SIN-1.
Figure 10D:
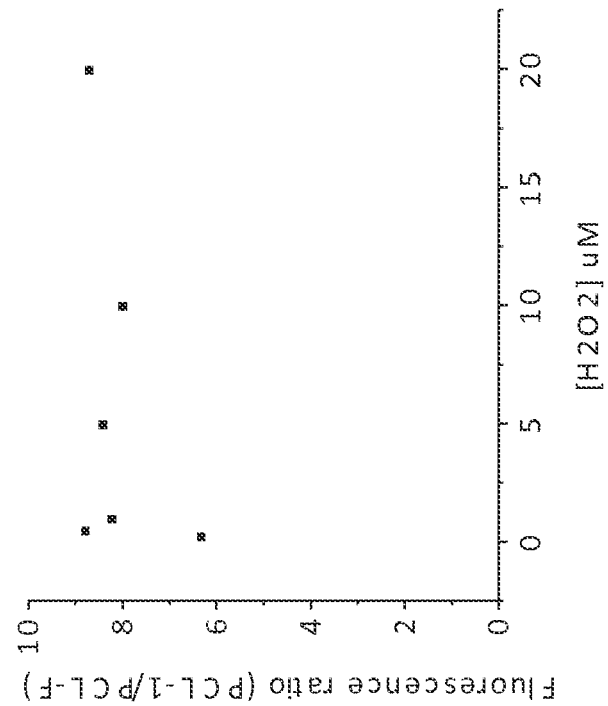
FIGS. 10C and 10D show fluorescence and fluorescence ratios of PCL-1 and PCL-F exposed to varying concentrations of $H_2O_2$.
Figure 10C:
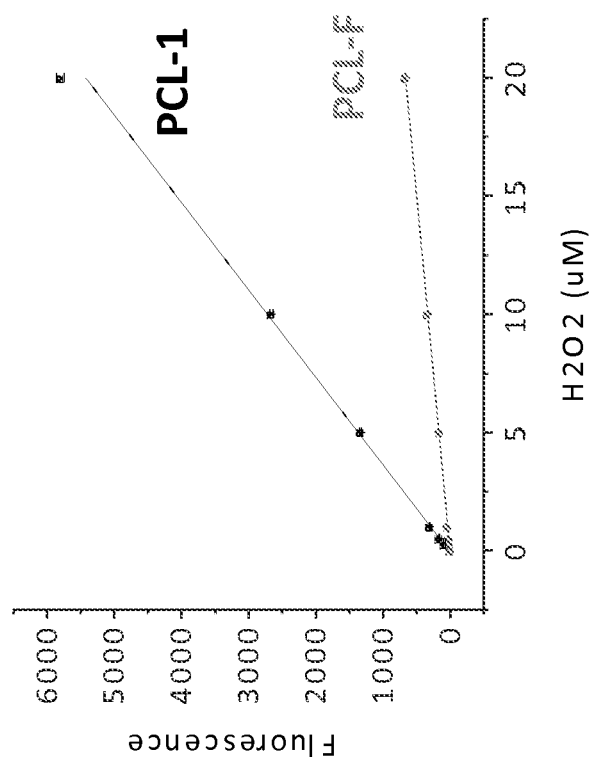

FIG. 9B shows fluorescence emission spectra of PCL-1 and PCL-F (Ex. 325 nm). FIGS. 9C and 9D show absorption at 268 nm as a function of pH for model complexes of PCL-1 (4-hydroxymethylphenylboronic acid) and PCL-F (2-fluoro-4-hydroxymethylphenylboronic acid) in determination of pK$_a$ of the boronic acid functionality. Data were obtained in 100 mM sodium phosphate buffer containing 5% DMSO. FIG. 10A shows a plot of fluorescence (Ex. 325, Em. 535) of PCL-1 and PCL-F (5 μM) exposed to varying concentrations of SIN-1 for 90 minutes at 37° C. and FIG. 10B shows the fluorescence ratio, PCL-1/PCL-F, at varying concentrations of SIN-1 for 90 minutes at 37° C. FIGS. 10C and 10D show fluorescence and fluorescence ratios of PCL-1 and PCL-F (5 μM) exposed to varying concentrations of $H_2O_2$ for 90 minutes at 37° C. Experiments were performed in 100 mM sodium phosphate buffer at pH 8.5, containing 5% DMSO.

Figures 11A, 11B:
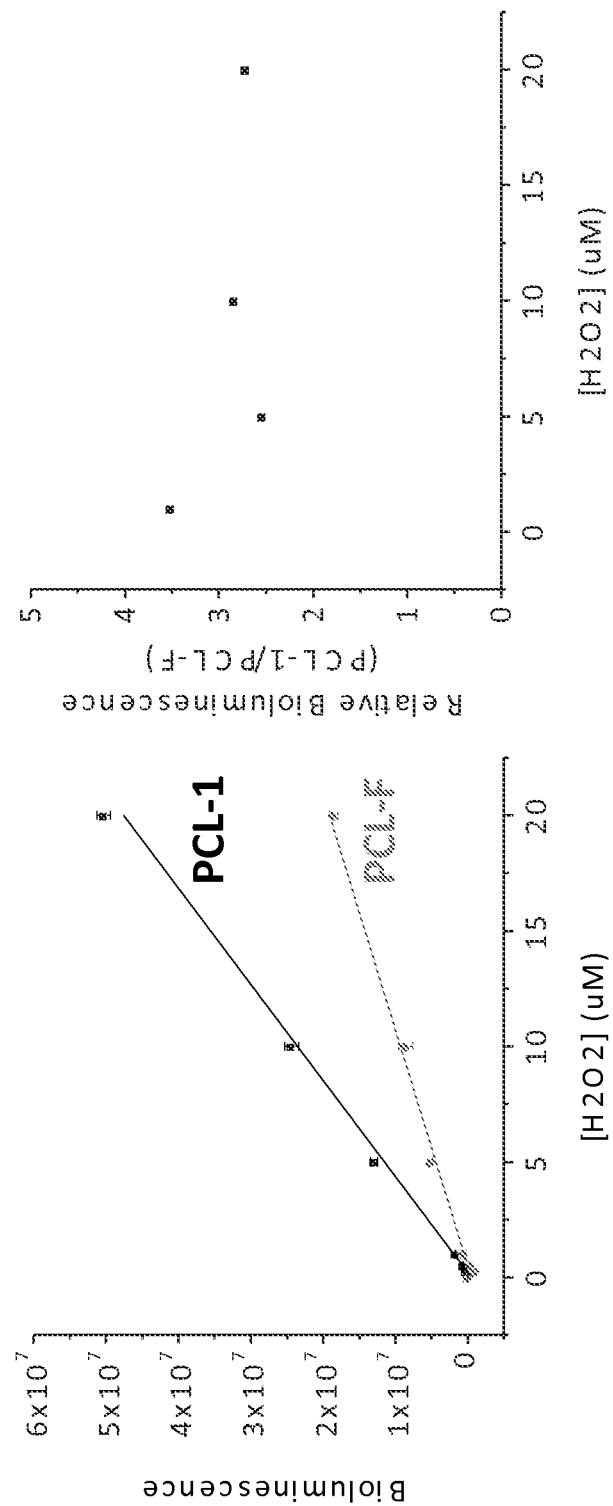
FIG. 11A shows bioluminescence of PCL-1 and PCL-F exposed to varying concentrations of SIN-1 and FIG. 11B shows the bioluminescence ratio, PCL-1/PCL-F, at varying concentrations of SIN-1.
Figures 11C, 11D:
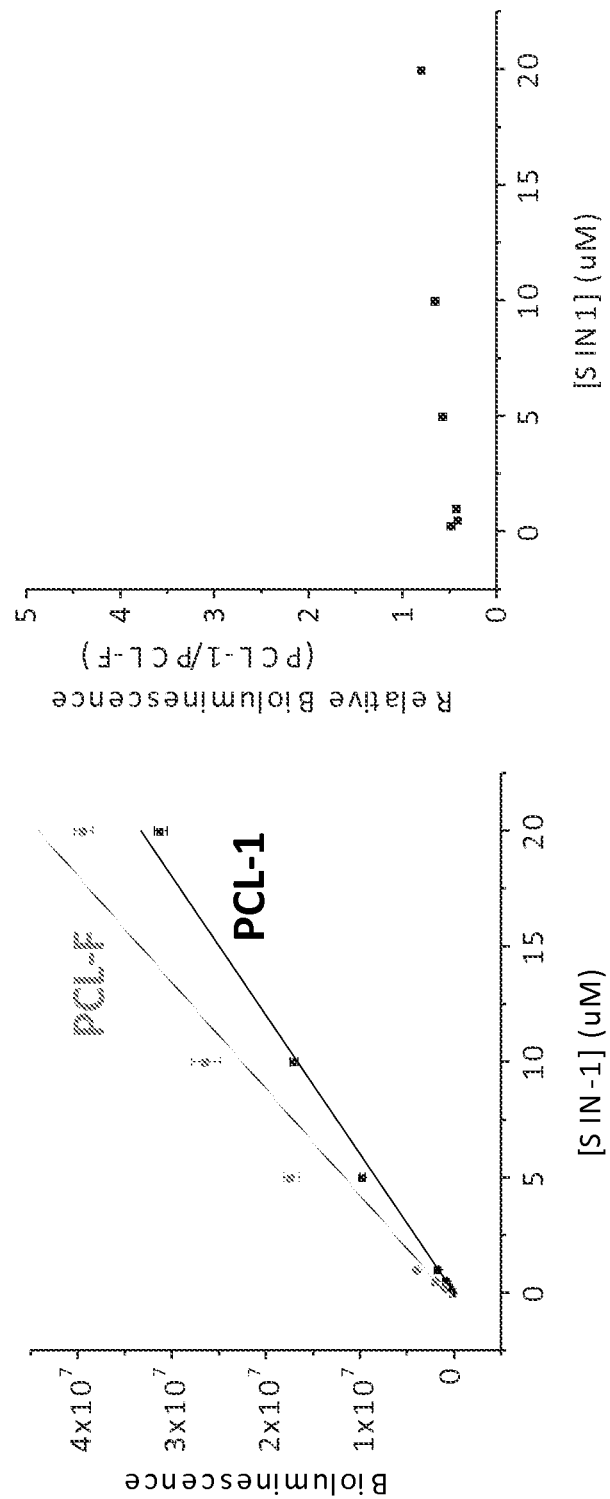
FIGS. 11C and 11D show bioluminescence and bioluminescence ratios of PCL-1 and PCL-F exposed to varying concentrations of $H_2O_2$.

FIG. 11A shows the bioluminescence of PCL-1 and PCL-F exposed to varying concentrations of SIN-1 for 90 minutes at 37° C., followed by treatment with 100 μg/mL recombinant luciferase in 100 mM sodium phosphate containing 10 mM MgCl$_2$ and 2 mM ATP at pH 7.4 and integration of luminescence at 612 nm over 60 minutes. FIG. 11B shows the bioluminescence ratio, PCL-1/PCL-F, at varying concentrations of SIN-1. FIGS. 11C and 11D show bioluminescence and bioluminescence ratios of PCL-1 and PCL-F exposed to varying concentrations of H$_2$O$_2$ under the same conditions. These data demonstrate a distinct fluorescence and bioluminescence response for PCL-1/PCL-F to peroxynitrite as compared to hydrogen peroxide.

Figures 12A, 12B:
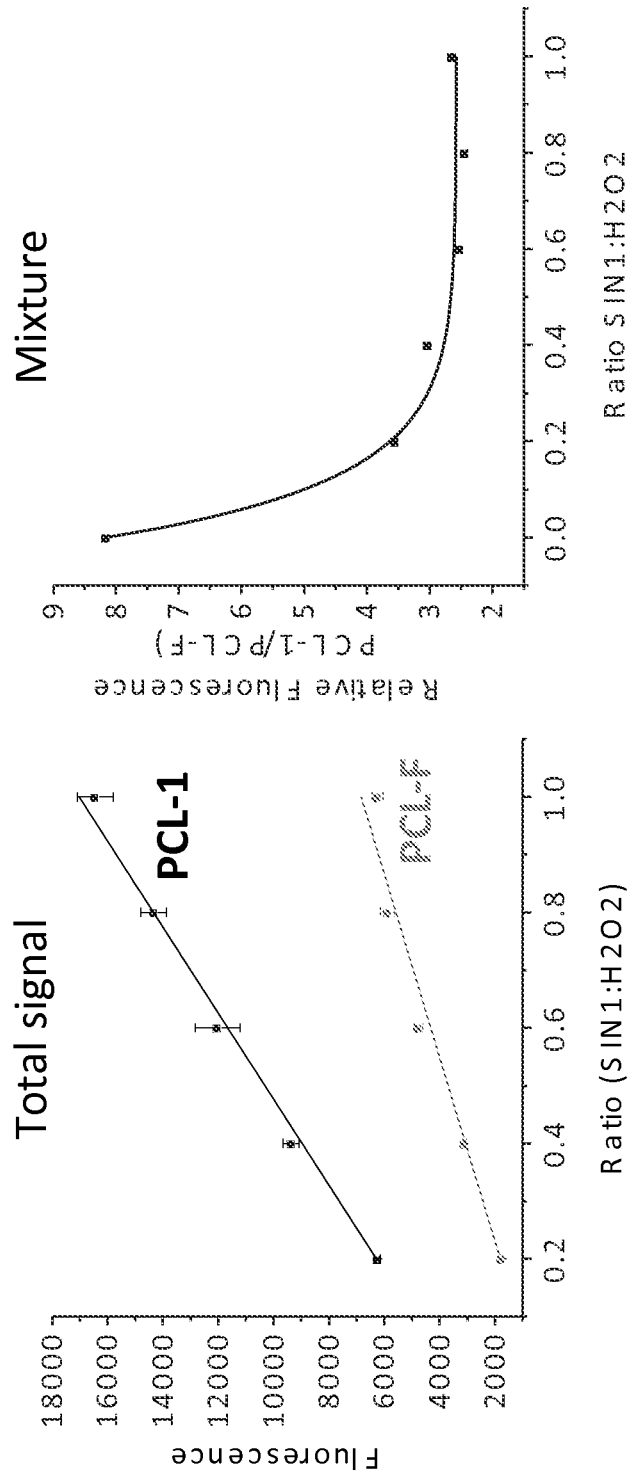
FIG. 12A shows fluorescence of PCL-1 and PCL-F at varying SIN-1/$H_2O_2$ ratios.
FIG. 12B shows the fluorescence ratio, PCL-1/PCL-F, at varying SIN-1/$H_2O_2$ ratios.
Figure 13:
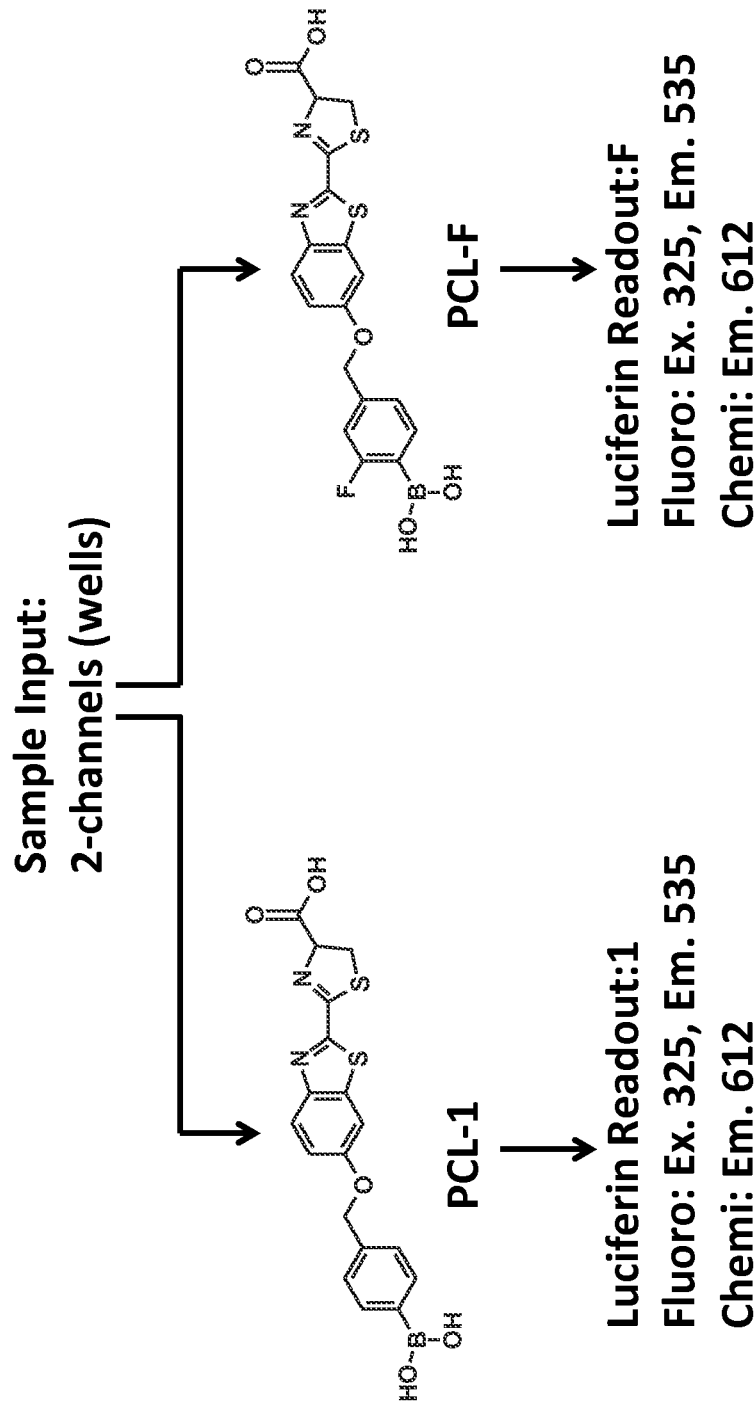
FIG. 13 shows the experimental design of a 2-well ratiometric assay for dual detection of hydrogen peroxide and peroxynitrite. In this assay, fluorescence of PCL-1 and PCL-F was detected in separate wells.

Because of the distinct reactivity characteristics of PCL-F and PCL-1 toward the investigated oxidants, the amount of peroxynitrite in a sample relative to the amount of H$_2$O$_2$ can be determined by measuring the relative fluorescence (i.e. the fluorescence ratio) of PCL-1 to PCL-F, as shown in FIGS. 12A and 12B.

Other absorbance, fluorometric, and kinetic parameters of PCL-1 and PCL-F are shown in Table 3. These parameters further demonstrate significantly higher selectivity for peroxynitrite over H$_2$O$_2$ of PCL-F compared to PCL-1 ($k_{ONOO-}/k_{H2O2}$=40.9 for PCL-F, compared to $k_{ONOO-}/k_{H2O2}$=8.2 for PCL-1), regardless of the fact that PCL-F reacts slightly slower than PCL-1. These differences in selectivity can thus be useful for using PCL-F and PCL-1 for ratiometric detection of both H$_2$O$_2$ and peroxynitrite in a single experiment.

TABLE 3

Spectrophotometric, fluorometric, and kinetic parameters of PCL-F as compared to PCL-1.

| Cmpd. | $\lambda_{max}$ (nm) ($\epsilon$ (M$^{-1}$cm$^{-1}$))* | Fluor. max* (Ex$_{325}$) | pKa$_{B(OH)2}$ | $\delta^{11}$B (ppm)** | $k_{H2O2}$ (M$^{-1}$s$^{-1}$)*** | $k_{ONOO-}$ (M$^{-1}$s$^{-1}$)*** |
|---|---|---|---|---|---|---|
| PCL-1 | 328 (19448) | 435 | 8.9 | 29.3 | 1.2 (±0.3) | 9.8 (±0.1) × 10$^5$ |
| PCL-F | 328 (19648) | 435 | 7.8 | 28.7 | 0.11 (±0.02) | 4.5 (±0.2) × 10$^5$ |

*Spectral parameters determined in 100 mM sodium phosphate, pH 7.4 containing 5% DMSO (v/v).
**$^{11}$B-NMR chemical shift determined using analog compounds for PCL-1 and PCL-F (4-hydroxymethylphenylboronic acid and 2-fluoro-4-hydroxymethylphenylboronic acid, respectively) in D$_2$O, referenced to external standard B(OH)$_3$ at pH 2.0 ($\delta$ = 19.6 ppm).
***k values determined in 100 mM sodium phosphate, pH 7.4, 37° C.

Example 10

Ratiometric Assays

Figure 14:
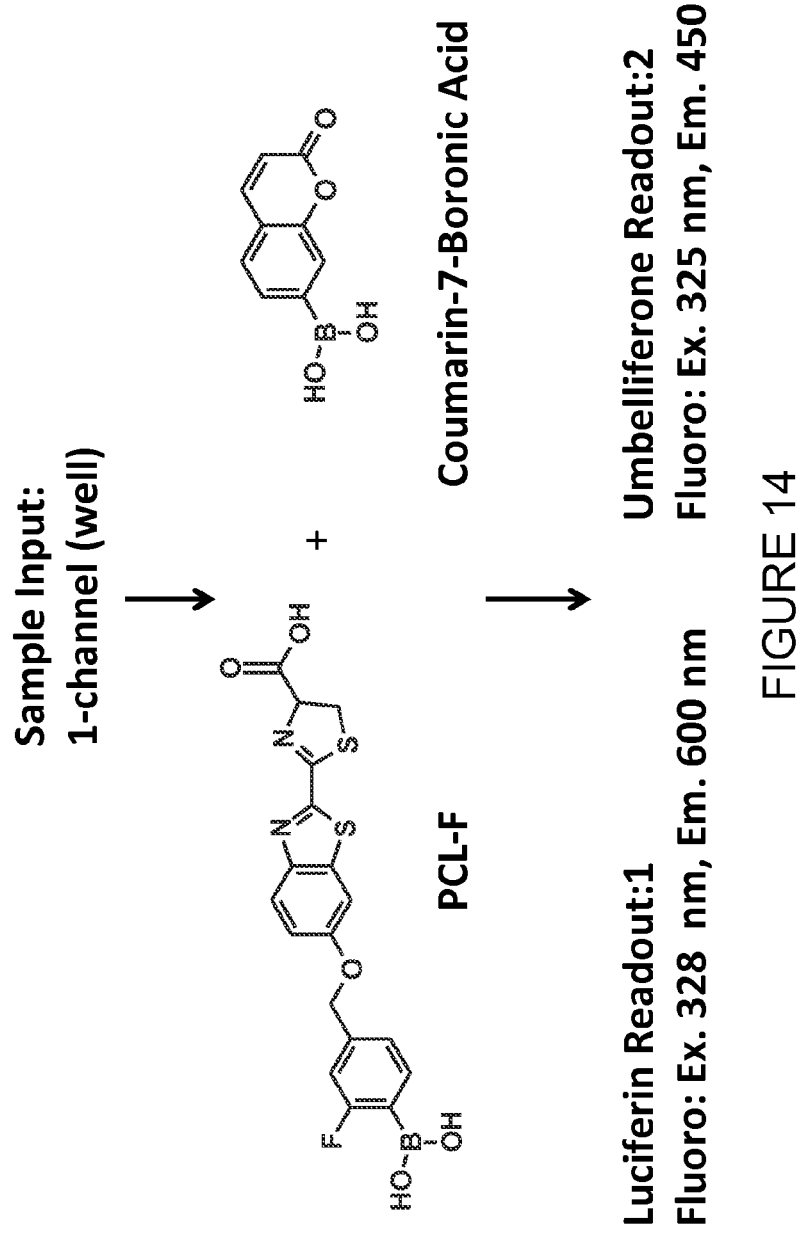
FIG. 14 shows the experimental design of a 1-well ratiometric assay for dual detection of hydrogen peroxide and peroxynitrite. In this assay, fluorescence of coumarin-7-boronic acid (CBA) (which becomes umbelliferone, also called 7-hydroxycoumarin, after reaction with hydrogen peroxide or peroxynitrite) and PCL-F (which becomes luciferin after reaction with hydrogen peroxide or peroxynitrite) were detected in the same well.
Figure 15:
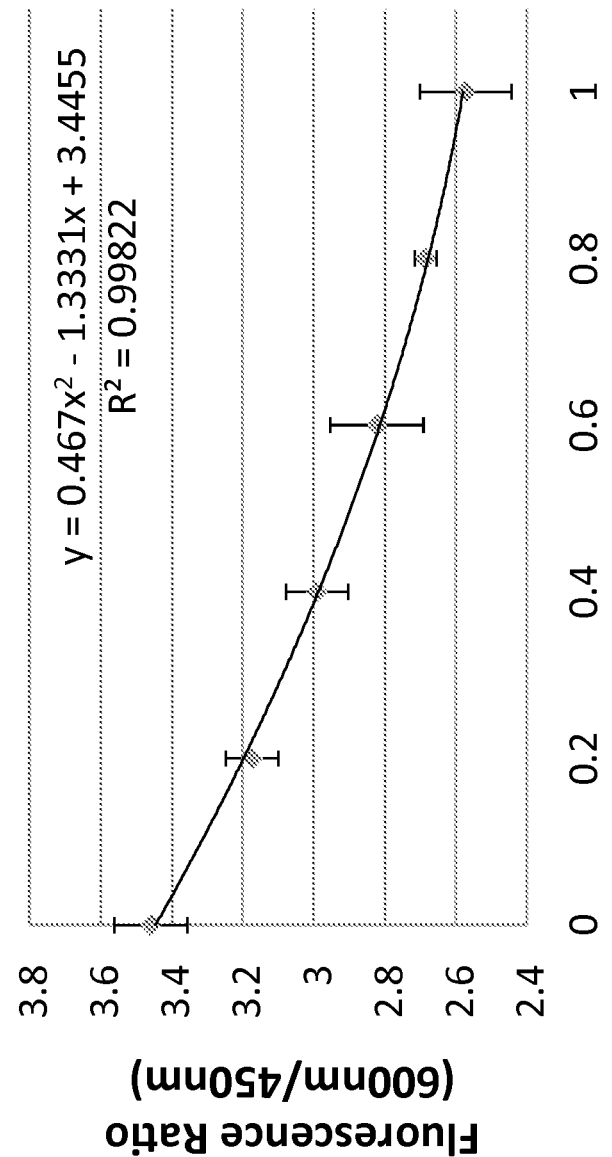
FIG. 15 shows the fluorescence ratio, CBA/PCL-F, at varying mole ratios of ONOO$^-$/$H_2O_2$.

FIGS. 14 and 15 show experimental designs of ratiometric assays for dual detection of hydrogen peroxide and peroxynitrite using PCLs. When the two fluorescent reagents used in the assay are PCL-1 and PCL-F, two wells are used because fluorescence of both PCL-1 and PCL-F are detected at the same wavelength of 535 nm.

When the two reagents used in the assay are PCL-F and coumarin-7-boronic acid (CBA), one well is used for the assay (that is, both fluorophores are detected in the same reaction mixture) because fluorescence of luciferin and umbelliferone are detected at different wavelengths.

FIG. 15 shows the fluorescence ratio of umbelliferone (from CBA) to luciferin (from PCL-F) measured in a single-well ratiometric assay at various mole ratios of peroxynitrite to hydrogen peroxide. The data were collected at a CBA concentration of 10 μM, a PCL-F concentration of 10 μM, a total oxidant concentration (ONOO$^-$ concentration+ H$_2$O$_2$ concentration) of 10 μM, in 100 mM TRIS buffer at pH 8.0 and 37° C. after a reaction time of 90 minutes.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, can be made without departing from the spirit and scope thereof.

What is claimed is:

1. A compound of formula (I),

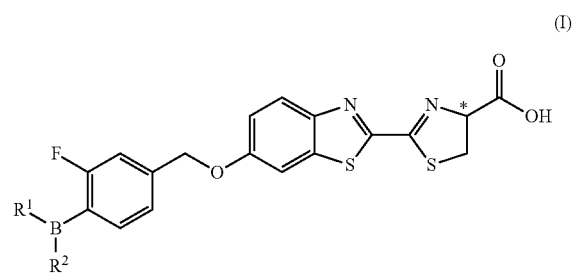

(I)

or a pharmaceutically acceptable salt, ester, amide, prodrug, or radiolabeled form thereof, wherein R$^1$ and R$^2$ are each independently hydroxy or alkoxy, or R$^1$ and R$^2$ form together with the boron atom to which they are attached an optionally substituted 5- to 7-membered dioxaborolanyl group; and wherein * designates a stereocenter.

2. The compound of claim 1, wherein

R$^1$ is hydroxy; and

R$^2$ is hydroxy.

3. The compound of claim 1, wherein

R$^1$ is alkoxy; and

R$^2$ is alkoxy.

4. The compound of claim 1, wherein R$^1$ and R$^2$ form together with the boron atom to which they are attached an optionally substituted 5- to 7-membered dioxaborolanyl group.

5. The compound of claim 4, wherein R$^1$ and R$^2$ form together with the boron atom to which they are attached a 4,4,5,5-tetramethyl-1,3,2-dioxaborolan-2-yl group.

6. The compound of claim 1 wherein * designates a stereocenter having the (S)-configuration.

7. The compound of claim 1 wherein * designates a stereocenter having the (R)-configuration.

8. The compound of claim 1, having formula (I-A),

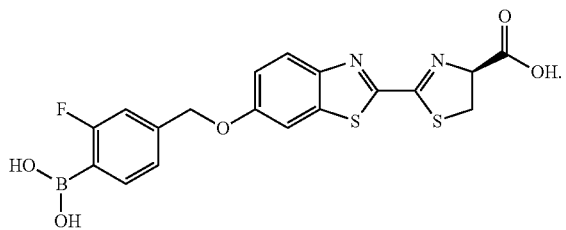
(I-A)

9. The compound of claim 1, having formula (I-B)

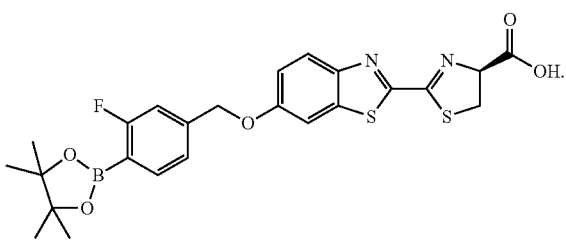
(I-B)

10. A method of detecting one or more oxidants in a cell or tissue comprising:
(a) contacting the cell or tissue with an effective amount of one or more compounds of formula (I):

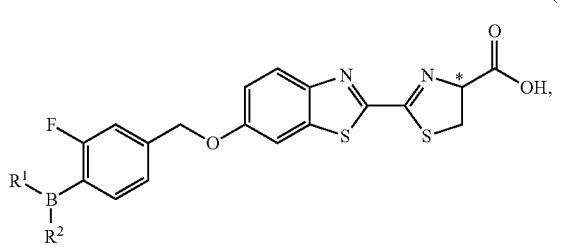
(I)

or a pharmaceutically acceptable salt, ester, amide, prodrug, or radiolabeled form thereof,
wherein $R^1$ and $R^2$ are each independently hydroxy or alkoxy, or $R^1$ and $R^2$ form together with the boron atom to which they are attached an optionally substituted 5- to 7-membered dioxaborolanyl group, and wherein * designates a stereocenter; and
(b) detecting a signal generated by reaction of the one or more compounds of formula (I) with the one or more oxidants.

11. The method of claim 10, wherein the one or more compounds of formula (I) comprise formula (I-A),

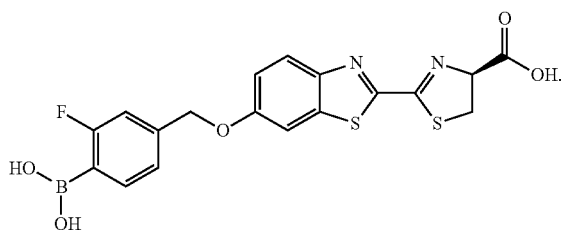
(I-A)

12. The method of claim 10, wherein the one or more compounds of formula (I) comprise PCL-F:

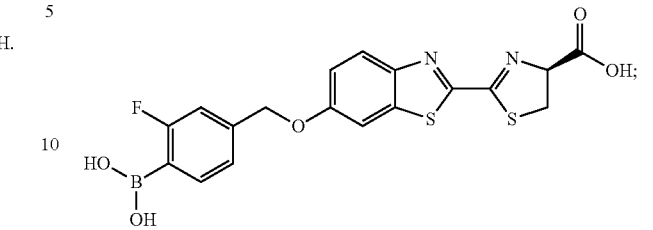
(PCL-F)

the method further comprising contacting the cell or tissue with an effective amount of PCL-1:

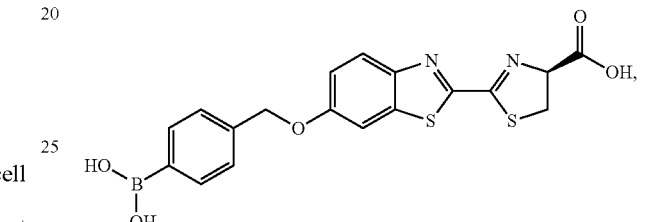
(PCL-1)

and detecting a signal generated by reaction of PCL-1 with the one or more oxidants.

13. The method of claim 10, wherein the one or more oxidants comprise peroxynitrite.

14. The method of claim 10, wherein the one or more oxidants comprise hydrogen peroxide.

15. The method of claim 10, wherein the one or more oxidants comprise peroxynitrite and hydrogen peroxide.

16. The method of claim 10,
wherein the one or more compounds of formula (I) comprise PCL-F:

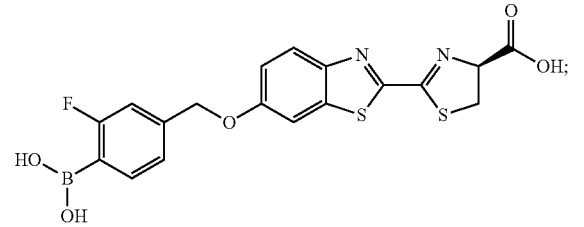
(PCL-F)

the method further comprising contacting the cell or tissue with an effective amount of coumarin-7-boronic acid (CBA) and detecting a signal generated by reaction of CBA with the one or more oxidants.

17. A method of detecting radiation-induced gastrointestinal injury in a subject comprising:
(a) administering to the subject one or more compounds according to claim 1; and
(b) detecting a signal generated by reaction of the one or more compounds according to claim 1 with peroxynitrite in the feces of the subject.

18. A method of detecting radiation-induced gastrointestinal injury in a subject comprising:
(a) administering to the subject PCL-1:
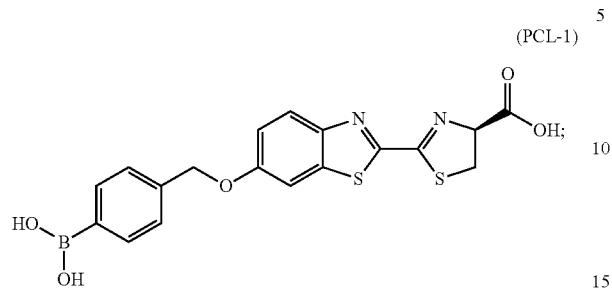
and
(b) detecting a signal generated by reaction of PCL-1 with peroxynitrite in the feces of the subject.
* * * * *